US010617291B2

(12) United States Patent
Casson

(10) Patent No.: US 10,617,291 B2
(45) Date of Patent: Apr. 14, 2020

(54) MEDICAL DEVICE WITH AN AIRWAY INSERTION MEMBER

(71) Applicant: INSCOPE MEDICAL SOLUTIONS, INC., Louisville, KY (US)

(72) Inventor: Adam Casson, Louisville, KY (US)

(73) Assignee: INSCOPE MEDICAL SOLUTIONS, INC., New Albany, IN (US)

(*) Notice: Subject to any disclaimer, the term of this patent is extended or adjusted under 35 U.S.C. 154(b) by 150 days.

(21) Appl. No.: 15/747,132

(22) PCT Filed: Aug. 3, 2016

(86) PCT No.: PCT/US2016/045299
§ 371 (c)(1),
(2) Date: Jan. 23, 2018

(87) PCT Pub. No.: WO2017/024007
PCT Pub. Date: Feb. 9, 2017

(65) Prior Publication Data
US 2018/0214013 A1    Aug. 2, 2018

Related U.S. Application Data

(60) Provisional application No. 62/201,545, filed on Aug. 5, 2015.

(51) Int. Cl.
*A61B 1/267* (2006.01)
*A61B 1/015* (2006.01)
(Continued)

(52) U.S. Cl.
CPC .......... *A61B 1/267* (2013.01); *A61B 1/00094* (2013.01); *A61B 1/015* (2013.01);
(Continued)

(58) Field of Classification Search
CPC ................................ A61B 1/015; A61B 1/267
See application file for complete search history.

(56) References Cited

U.S. PATENT DOCUMENTS 3,848,587 A    11/1974   McDonald
5,702,351 A    12/1997   Bar-Or et al.
(Continued)

FOREIGN PATENT DOCUMENTS

AU    2015210829 A1    8/2016
CA       2937890 A1    8/2015
(Continued)

OTHER PUBLICATIONS

International Preliminary Report on Patentability for PCT/US2016/045299 dated Feb. 6, 2018, 11 pages.
(Continued)

*Primary Examiner* — Christian A Sevilla
(74) *Attorney, Agent, or Firm* — Nixon Peabody LLP

(57) ABSTRACT

Disclosed are laryngoscopes and other devices that include both a visualization feature and a suction component, to eliminate debris and bodily fluids and secretions that may accumulate on the visualization component. The devices may include one or more of the fluid intake ports that may be sized and located proximate to the operational ends of the visual-aid components, e.g., the camera lens or LED, to maintain a clean field of view for operation of the component. The internal passageways of the device are configured, dimensioned and/or shaped to facilitate desired fluid flow characteristics, flow rate, and/or pressure rates and facilitate methods of manufacturing the device.

61 Claims, 20 Drawing Sheets

FIG. 2

(51) Int. Cl.
  *A61B 1/05* (2006.01)
  *A61B 1/12* (2006.01)
  *A61B 1/00* (2006.01)
  *A61B 1/04* (2006.01)
  *A61B 1/06* (2006.01)
  *A61B 1/07* (2006.01)

(52) U.S. Cl.
  CPC .............. *A61B 1/05* (2013.01); *A61B 1/126* (2013.01); *A61B 1/042* (2013.01); *A61B 1/0684* (2013.01); *A61B 1/07* (2013.01)

(56) References Cited

U.S. PATENT DOCUMENTS

| | | | |
|---|---|---|---|
| 5,897,489 | A | 4/1999 | Urbanowicz et al. |
| 7,608,040 | B1 | 10/2009 | Dunst |
| 2001/0051766 | A1 | 12/2001 | Gazdzinski |
| 2002/0022769 | A1 | 2/2002 | Smith et al. |
| 2002/0082475 | A1 | 6/2002 | Stahl et al. |
| 2007/0287888 | A1 | 12/2007 | Lovell et al. |
| 2010/0121152 | A1 | 5/2010 | Boedeker |
| 2010/0256482 | A1 | 10/2010 | Peters et al. |
| 2010/0261968 | A1 | 10/2010 | Nearman et al. |
| 2011/0028790 | A1* | 2/2011 | Farr ............ A61B 1/00052 348/77 |
| 2011/0092773 | A1 | 4/2011 | Goldstein |
| 2011/0130627 | A1 | 6/2011 | McGrail et al. |
| 2011/0178372 | A1 | 7/2011 | Pacey et al. |
| 2012/0035502 | A1 | 2/2012 | Menegazzi |
| 2012/0289858 | A1* | 11/2012 | Ouyang ............ A61B 10/0275 600/562 |
| 2013/0060090 | A1 | 3/2013 | McGrath et al. |
| 2013/0104884 | A1 | 5/2013 | Vazales et al. |
| 2013/0197312 | A1 | 8/2013 | Miller et al. |
| 2016/0000300 | A1 | 1/2016 | Williams |
| 2016/0345803 | A1 | 12/2016 | Mallory et al. |

FOREIGN PATENT DOCUMENTS

| | | |
|---|---|---|
| CA | 3015226 A1 | 9/2017 |
| CN | 1452472 A | 10/2003 |
| CN | 102481086 A | 5/2012 |
| CN | 106132281 A | 11/2016 |
| CN | 108697318 A | 10/2018 |
| EP | 3099216 A1 | 12/2016 |
| EP | 3331420 A | 6/2018 |
| EP | 3422925 A1 | 1/2019 |
| JP | 2017504465 A | 2/2017 |
| MX | 2016009802 A | 1/2017 |
| TH | 177022 A | 6/2018 |
| WO | 2012172076 A1 | 12/2012 |
| WO | 2014105649 A1 | 7/2014 |
| WO | 2015116900 A1 | 8/2015 |
| WO | 2017024007 A1 | 2/2017 |
| WO | 2017151796 A1 | 9/2017 |

OTHER PUBLICATIONS

EP Examination Report for EP 15743864.9 dated Jan. 22, 2019, 3 pages.
EP Extended Search Report for 15743864.9 dated Aug. 30, 2017, 6 pages.
International Search Report and Written Opinion for PCT/US2016/045299 dated Oct. 26, 2016, 13 pages.
International Search Report and Written Opinion for PCT/US2017/020242 dated May 15, 2017, 22 pages.
PCT/US2015/013690 International Search Report and Written Opinion dated May 6, 2015, 8 pages.
PCT/US2015/013690 International Preliminary Report on Patentability dated Aug. 2, 2016, 7 pages.
International Preliminary Report on Patentability for PCT/US2017/020242 dated Sep. 4, 2018.

* cited by examiner

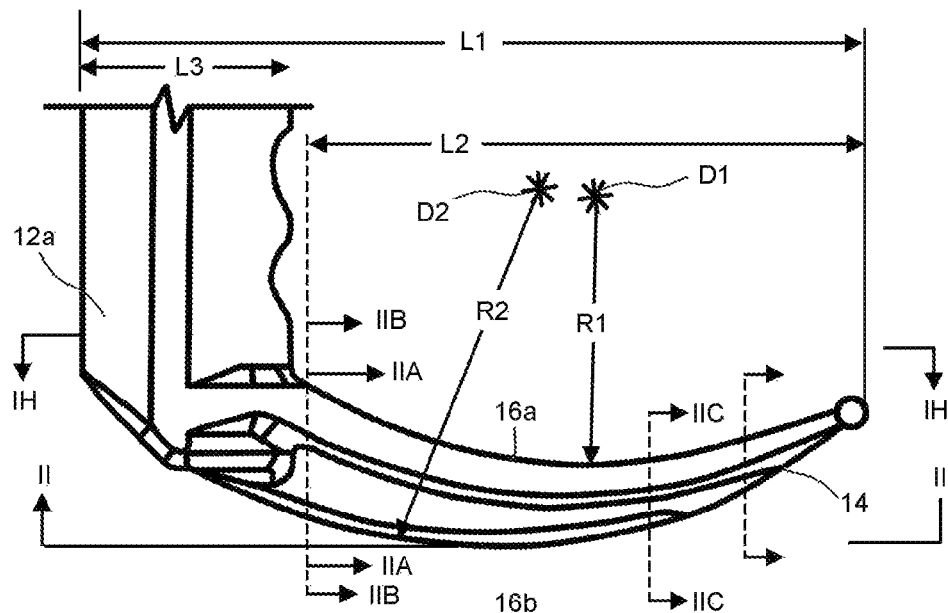
FIG. 1B
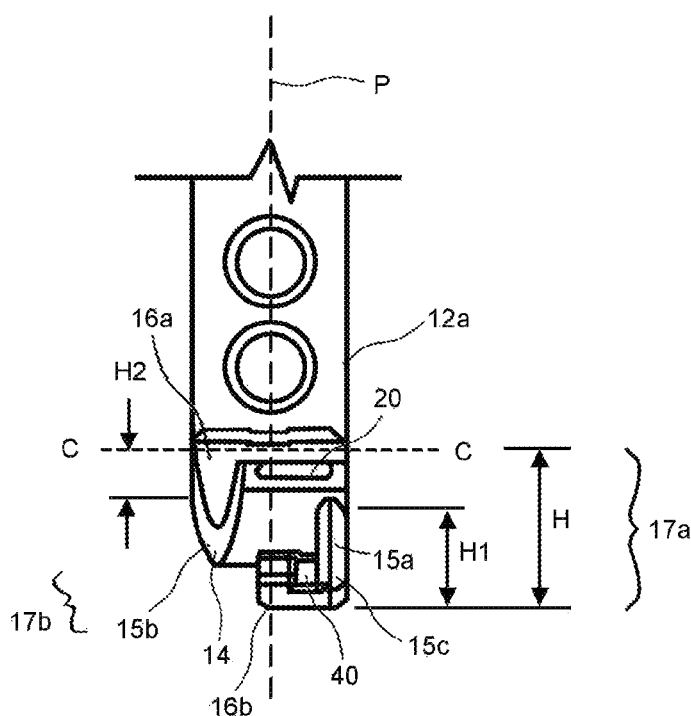
FIG. 1C
FIG. 1B-1C

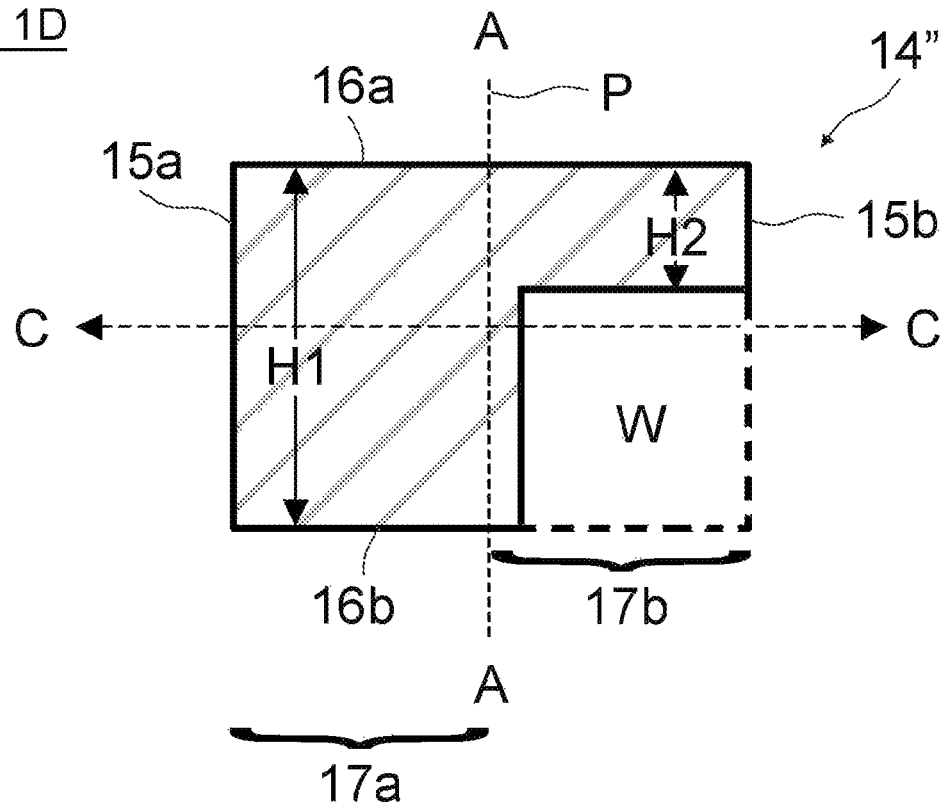
FIG. 1D
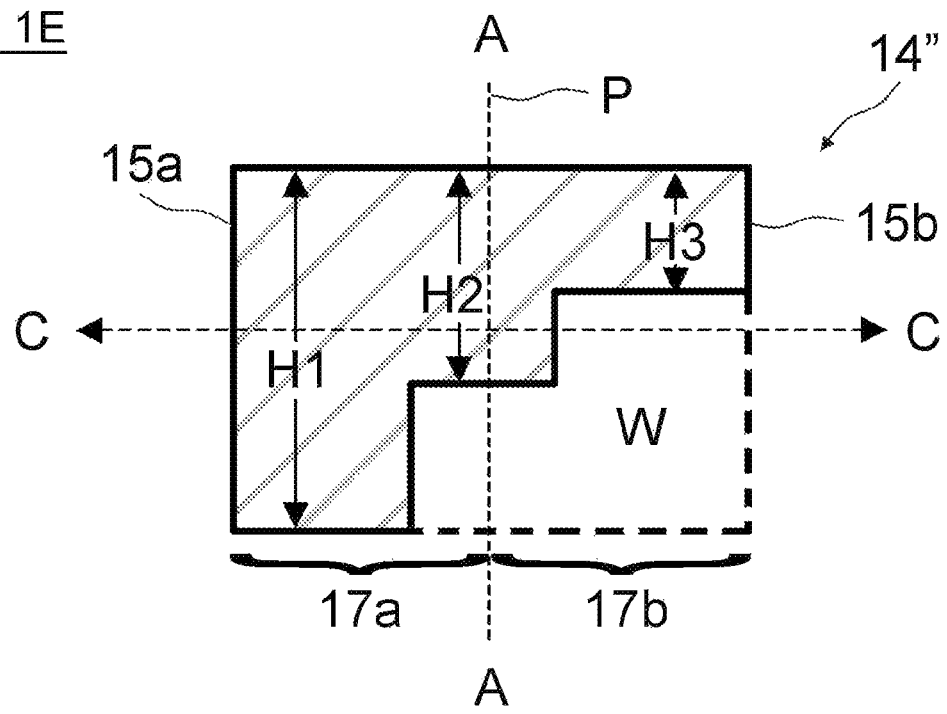
FIG. 1E
FIG. 1D-1E

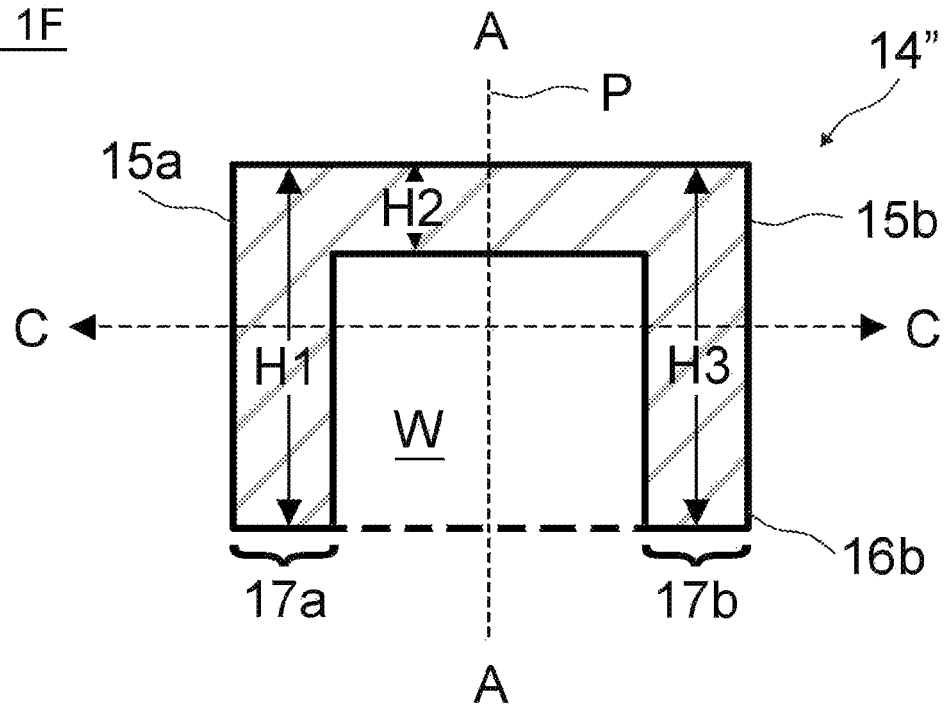
FIG. 1F
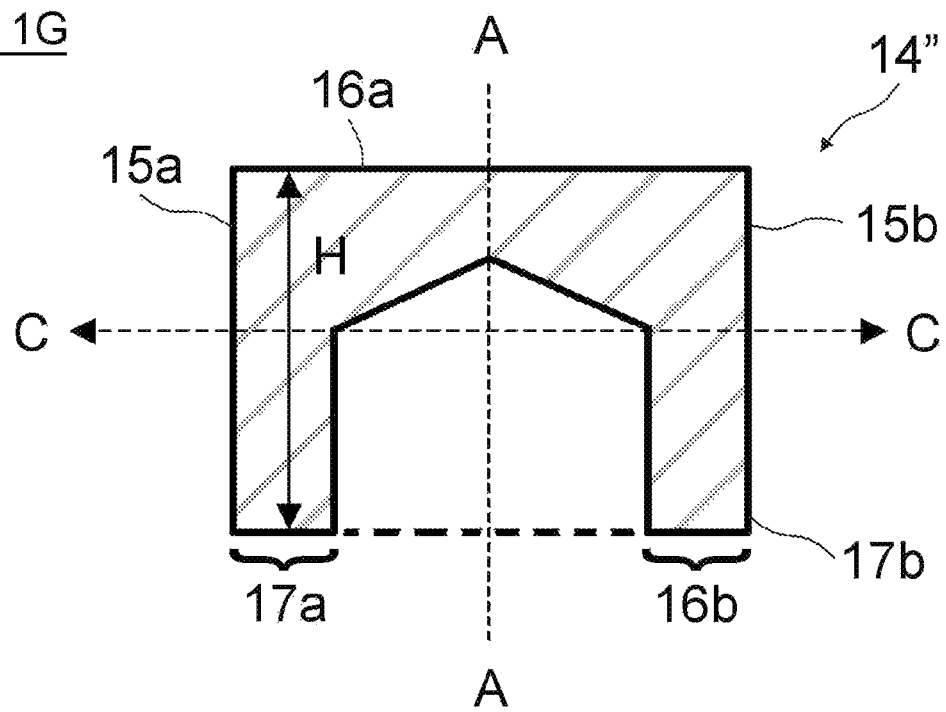
FIG. 1G
FIG. 1F-1G

FIG. 1H
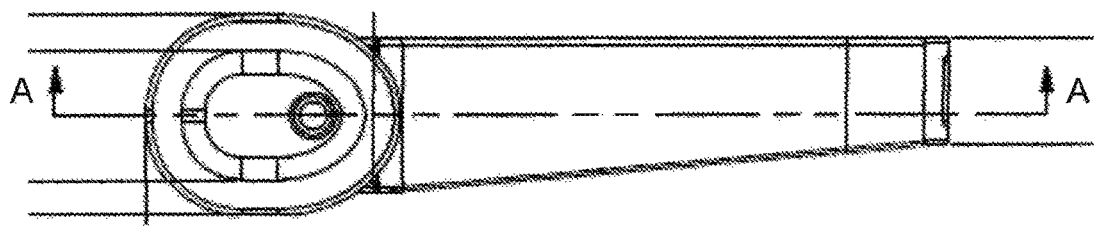
FIG. 1I
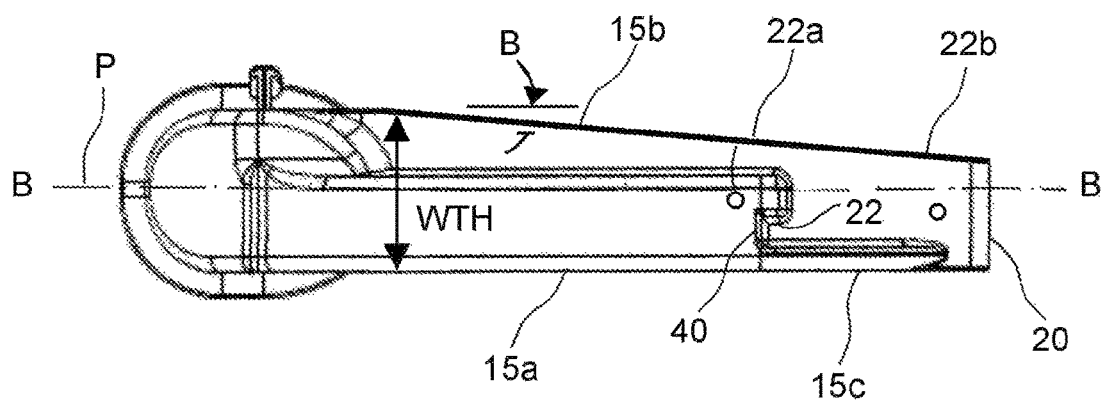
FIG. 1H-1I

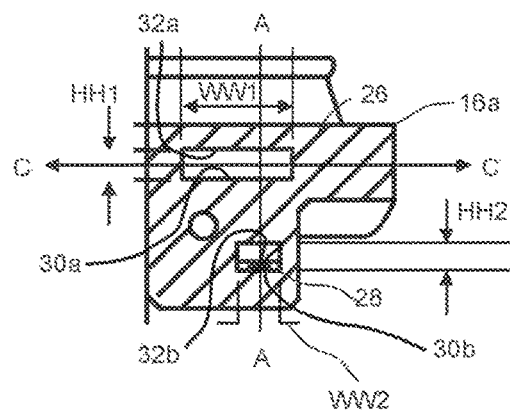
FIG. 2A
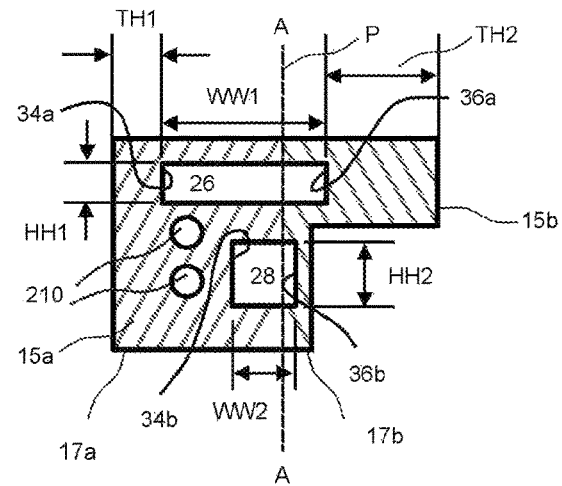
FIG. 2B
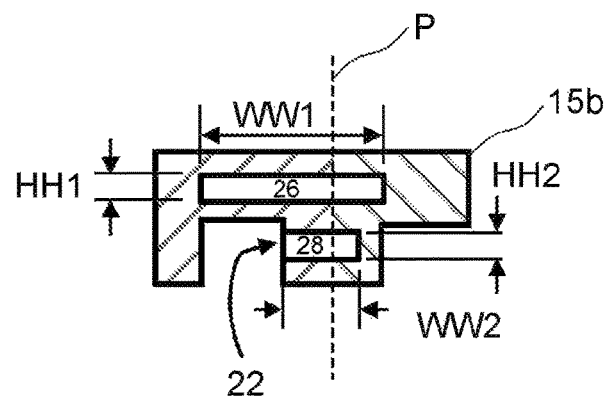
FIG. 2C
FIG. 2A-2C

FIG. 3A
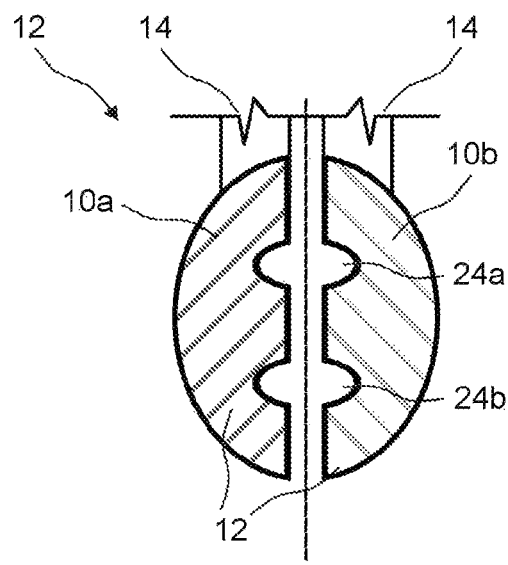
FIG. 3B
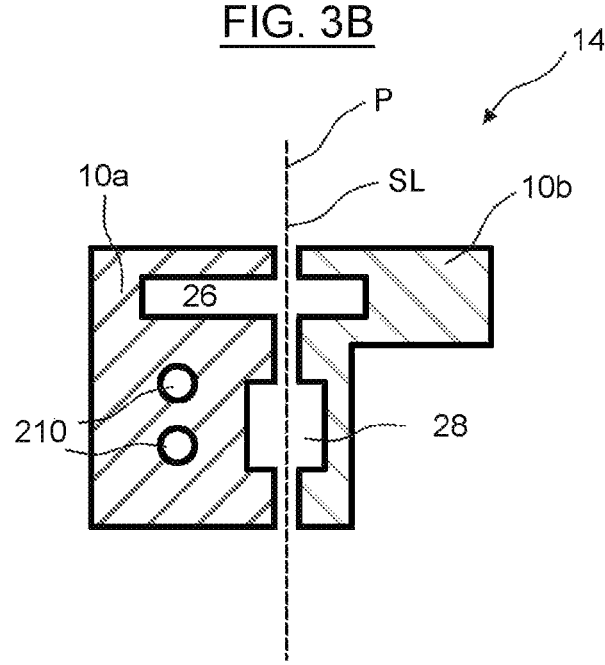
FIG. 3C
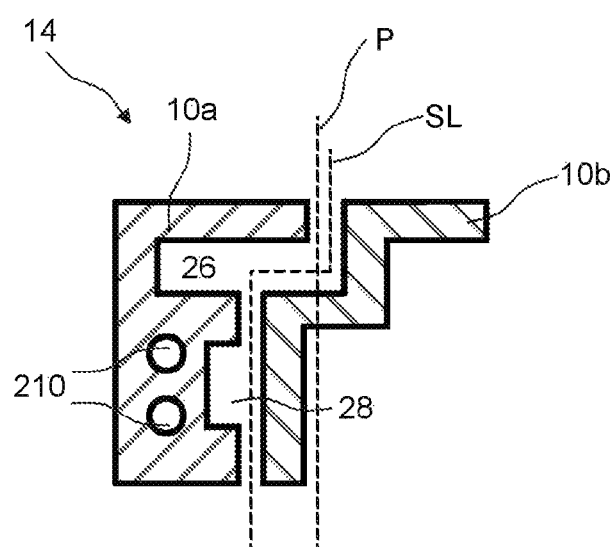
FIG. 3A-3C

FIG. 3D
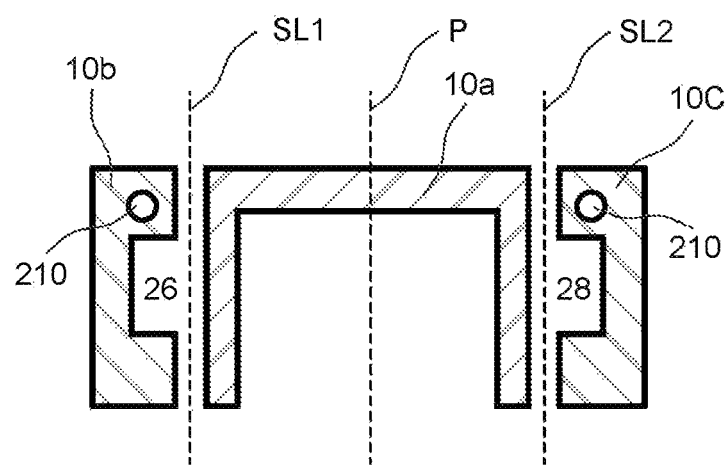
FIG. 3E
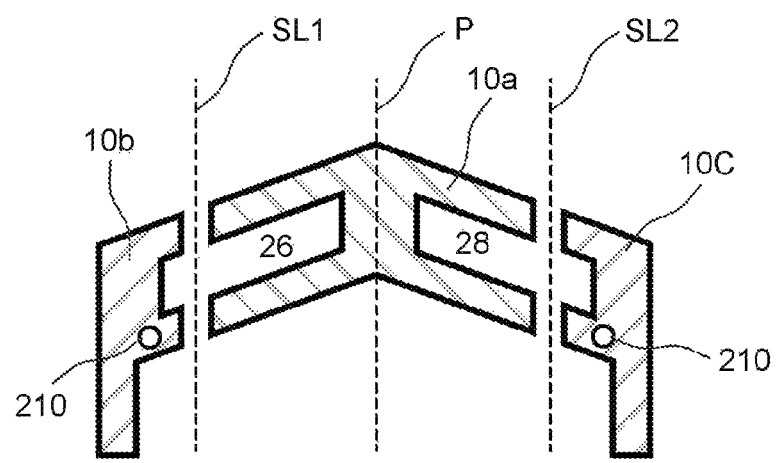
FIG. 3D-3E

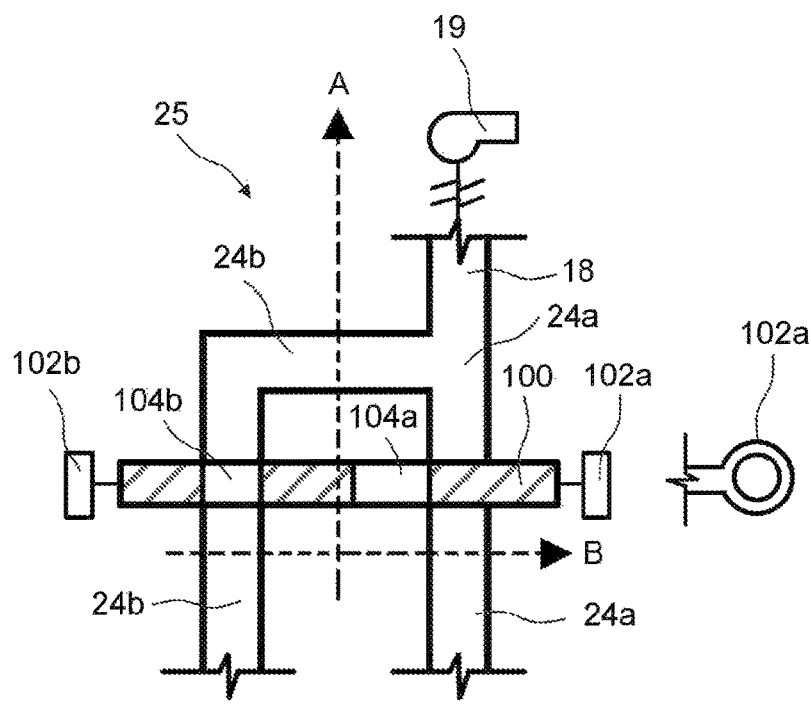
FIG. 4A
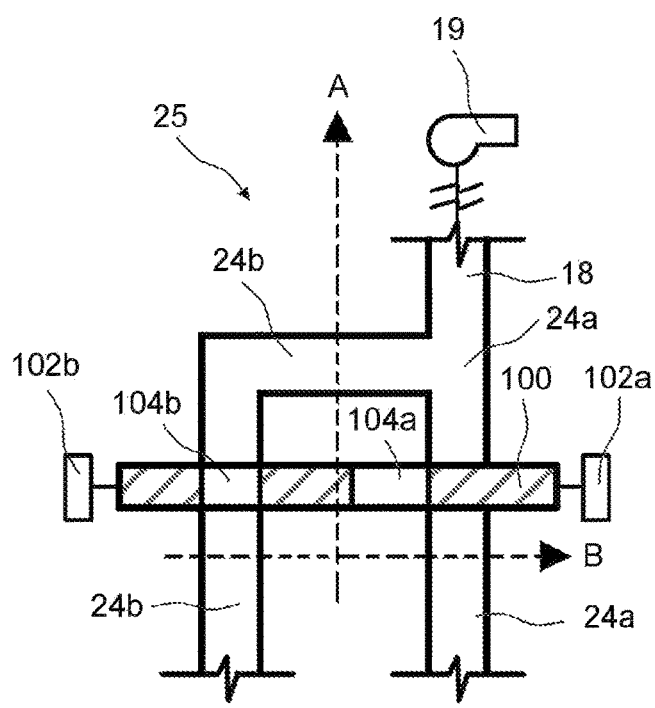
FIG. 4B
FIG. 4A-4B

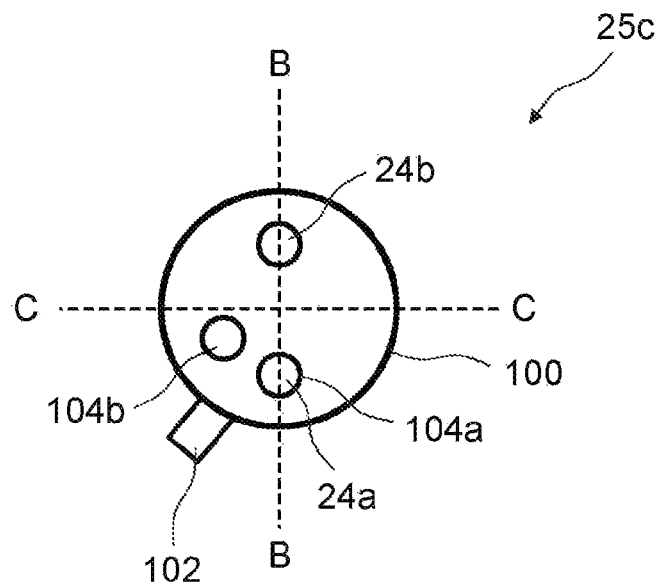
FIG. 4E
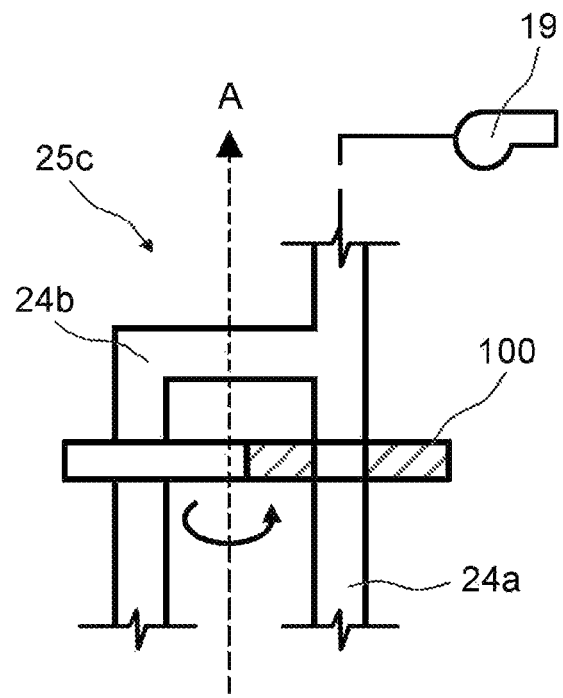
FIG. 4F
FIG. 4E-4F

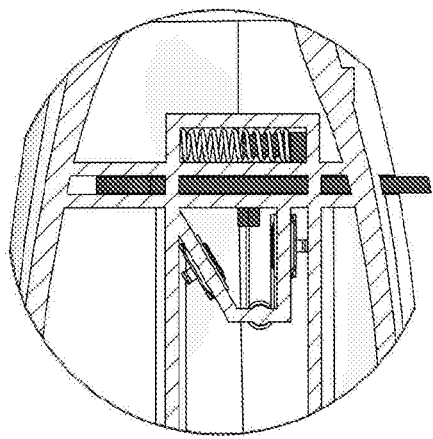
FIG. 7B
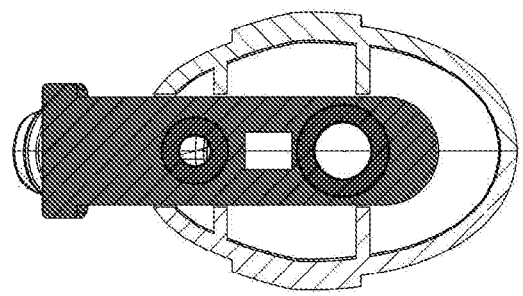
FIG. 7D
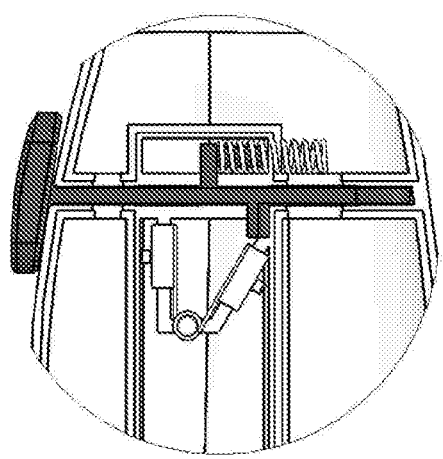
FIG. 7C
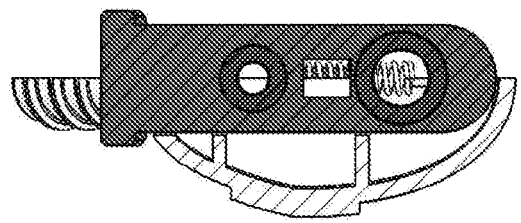
FIG. 7E
FIG. 7B-7E

MEDICAL DEVICE WITH AN AIRWAY INSERTION MEMBER

CROSS-REFERENCE TO RELATED APPLICATIONS

This application is a National Phase of International Application No. PCT/US2016/045299 filed Aug. 3, 2016, which designated the U.S. and that International Application was published under PCT Article 21(2) in English, which also includes a claim of priority under 35 U.S.C. § 119(e) to U.S. provisional patent application No. 62/201,545 filed Aug. 5, 2015, the entirety of which is hereby incorporated by reference.

FIELD

The present invention relates to medical devices with an airway insertion member such as, for example, devices for performing a laryngoscopy.

BACKGROUND

The following description includes information that may be useful in understanding the present invention. It is not an admission that any of the information provided herein is prior art or relevant to the presently claimed invention, or that any publication specifically or implicitly referenced is prior art.

Laryngoscopy is a medical procedure that is us to obtain a view of the vocal folds and the glottis. Laryngoscopy is an examination of the larynx (voice box) using a small mirror held just below the back of the palate, or a rigid or flexible viewing tube called a Laryngoscope placed in the mouth of the patient. Laryngoscopy may be performed to facilitate tracheal intubation during general anesthesia or cardiopulmonary resuscitation or for procedures on the larynx or other parts of the upper tracheobronchial tree.

There are two types of laryngoscopy including both (1) indirect laryngoscopy and (2) direct fiber-optic (flexible or rigid) laryngoscopy. Indirect laryngoscopy is performed whenever the provider visualizes the patient's vocal cords by a means other than obtaining a direct line of sight. For example during intubation, this may be facilitated by fiberoptic bronchoscopes, video laryngoscopes, fiberoptic stylets and mirror or prism optically-enhanced laryngoscopes.

Fiber-optic or direct laryngoscopy examinations allow doctors to see deeper into the throat by using either a flexible or rigid laryngoscope. Direct laryngoscopy is carried out usually the patient lying on his or her back; the laryngoscope is inserted into the mouth on the right side and flipped to the left to trap and move the tongue out of the line of sight, and, depending on the type of blade used, inserted either anterior or posterior to the epiglottis and then lifted with an upwards and forward motion ("away from you and towards the roof"). This move makes a view of the glottis possible. The doctor will examine the throat area through the scope's eyepiece.

There are at least ten different types of laryngoscope used for this procedure, each of which has a specialized use for the otolaryngologist and medical speech pathologist. This procedure is most often employed by anesthetists for endotracheal intubation under general anesthesia, but also in direct diagnostic laryngoscopy with biopsy.

Tracheal intubation using a laryngoscope has been demonstrated to fail in up to 35% of patients with an unpredicted difficult airway. Problems in securing the airway are still the main contributors to anesthesia-related morbidity and mortality.

SUMMARY

During laryngoscope use in uncontrolled settings such as helicopters or ambulances, the flight nurse, paramedic, or the emergency physician may need to provide suction to the oropharynx before being able to visualize the target vocal cords for intubation, whether a direct visualization method or an indirect video assisted fiberoptic technique is used. Suctioning the airways requires the use of the right hand during the intubation procedure. The right hand toggles between the endotracheal tube and the suction catheter and causes delays in procedure completion. Moreover, the fiberoptic camera may become covered with blood during trauma intubation, which can render the technology useless.

Therefore, in the present state there is a need for an art to develop a laryngoscopy instrument that can be used together with suction and video enabled features, for better visualization. Accordingly, disclosed are laryngoscopes and other devices that include both a visualization feature and a suction component, to eliminate debris and bodily fluids and secretions that may accumulate on the visualization component.

For instance, an example device may include one or more internal visual-aid components, such as for example, lighting, video cameras or associated components to facilitate either direct or indirect visualization of, for example, the glottis and/or vocal cords, using the device. Additionally, the device may include one or more of the fluid intake ports that may be sized and located proximate to the operational ends of the visual-aid components, e.g., the camera lens or LED, to maintain a clean field of view for operation of the component. Application of the negative pressure or suction at the various ports may be controlled by a fluid control valve assembly or arrangement incorporated in the handle having, for instance, manually operated device, push-button, or controller for operating the fluid control assembly.

To provide for the fluid communication between the outlet and the various fluid ports of the blade and housing visual components, the device may include one, two or more internal passageways between the fluid ports and the outlet.

As a fluid conduit or flow path of the device, the internal passageways of the device are configured, dimensioned and/or shaped to facilitate desired fluid flow characteristics, flow rate, and/or pressure rates. For instance, non-circular channels (and especially square shaped channels) have been shown to be optimal for fluid flow of the secretions removed with suction in the present disclosure. Accordingly, in some examples, it was determined that a large square or elliptical channel proved to be the most optimal in terms of fluid flow in relation to the surface area or cross sectional area utilized by the fluid channels.

Moreover, the internal passageways of the device are located or arranged within the device to provide for the geometries or profiles of the blade previously described in order to facilitate preferred insertion and viewing of the glottis and/or vocal cards as described herein. Accordingly, as there is a limited amount of space in the airway for the laryngoscope, breathing tube, and space to view the trachea. The L-shape (rotated 90 degrees clockwise) of the laryngoscope blade, in some examples, has proven to be the best shape to maximize the viewing/tube passing "window" in the airway. To maintain that shape while integrating suction, the shape/location of the channels and inlets are rectangular channels in some embodiments, to maximize the cross sectional area usage efficiency that run through the blade and the bottom of the flange.

Additionally, the configurations, profiles, dimensions, shape and/or location of the passageways facilitate methods of formation and/or manufacturing of the device. Embodiments of the device may be made in a molding process in which two injection molded elements are formed and joined together. In most examples, it is difficult to injection mold the current blade shape and suction channels without splitting it into two halves along the longitudinal axis. Accordingly, the design of the device included lining up the suction channels so that at least one edge of the channel would line up with the split line. In some examples, the split line crosses the centerline of the scope in a couple places, which increases strength in critical areas. Additionally, "drafts" are included on all the walls, which are slight angles (0.5-1.5 deg) to allow the parts to easily exit the molds. For the suction channels, this results in greater channel height at the split lines relative to the outer walls of the channels. These features can also be included in the pathway for the electronic components.

In one preferred aspect, the device is configured for single use. Accordingly, the device 10 is preferably formed in a manner and from a material such that the device 10 is disposable.

In some examples, disclosed is a light switch that is integrated into the valve and suction control for the channels. For instance, the light switch may be a one-time use switch that requires the user to push the suction valve once to turn on the LED.

Additionally, disclosed is a handle design that is optimized to push the user's hand into a position where they can easily have leverage using just the palm of their hand and their four fingers, leaving the thumb free to operate the valve as needed. This also keeps the user from using the patient's teeth as leverage for lifting the top of the blade and generally makes the handle more comfortable to the user.

Many laryngoscopes have a semi-circular shape on the dorsal side of the tip of the blade to allow the user to better control the patient's tongue in the airway. However, in some examples, because the device includes integrated suction and the semi-circular shape could not fit, the device may include a roughened surface texture to give the physicians better control.

BRIEF DESCRIPTION OF THE DRAWINGS

The accompanying drawings, which are incorporated herein and constitute part of this specification, illustrate exemplary embodiments of the invention and, together with the general description given above and the detailed description given below, serve to explain the features of the preferred embodiments of the invention. It should be understood that the preferred embodiments are some examples of the invention as provided by the appended claims.

FIG. 1B is a side-view of the device of FIG. 1.

FIG. 1C is a distal end view of the device of FIG. 1.

FIGS. 1D-1G are schematic cross-sectional views of the blade for use in the device of FIG. 1.

FIGS. 1H-1I are plane views of the blade of FIG. 1B along lines IH-IH, II-II.

FIG. 2A is a cross-sectional view of the blade in FIG. 1B along line IIA-IIA.

FIG. 2B is schematic a cross-sectional view of the blade in FIG. 1B along line IIB-IIB.

FIG. 2C is a schematic cross-sectional view of the blade in FIG. 1B along line IIC-IIC.

FIGS. 3A-3E are various and alternate schematic assembly views of handle or blade portions of the device 10. FIG. 3A is a cross-sectional view of the assembly components of handle portions of the device 10. FIGS. 3B-3E are cross-sectional view of the assembly components of handle portions of the device 10.

FIGS. 4A-4F illustrate various embodiments of a fluid control assembly for use in the device of FIG. 1. FIGS. 4A-4C illustrate cross sectional views of an embodiment of a control assembly embodied as a gate valve. FIG. 4D-4F illustrate cross sectional views of embodiments of a control assembly embodied as a rotatable disc valve.

FIG. 6D is a cross sectional view of an embodiment of a laryngoscope device of FIG. 6A along the B-B axis.

FIG. 7B is a cross sectional view of an embodiment of a laryngoscope device.

FIG. 7C is a cross sectional view of an embodiment of a laryngoscope device.

FIG. 7D is a cross sectional view of an embodiment of a laryngoscope device.

FIG. 7E is a cross sectional view of an embodiment of a laryngoscope device.

DETAILED DESCRIPTION

Overview

Figure 1:
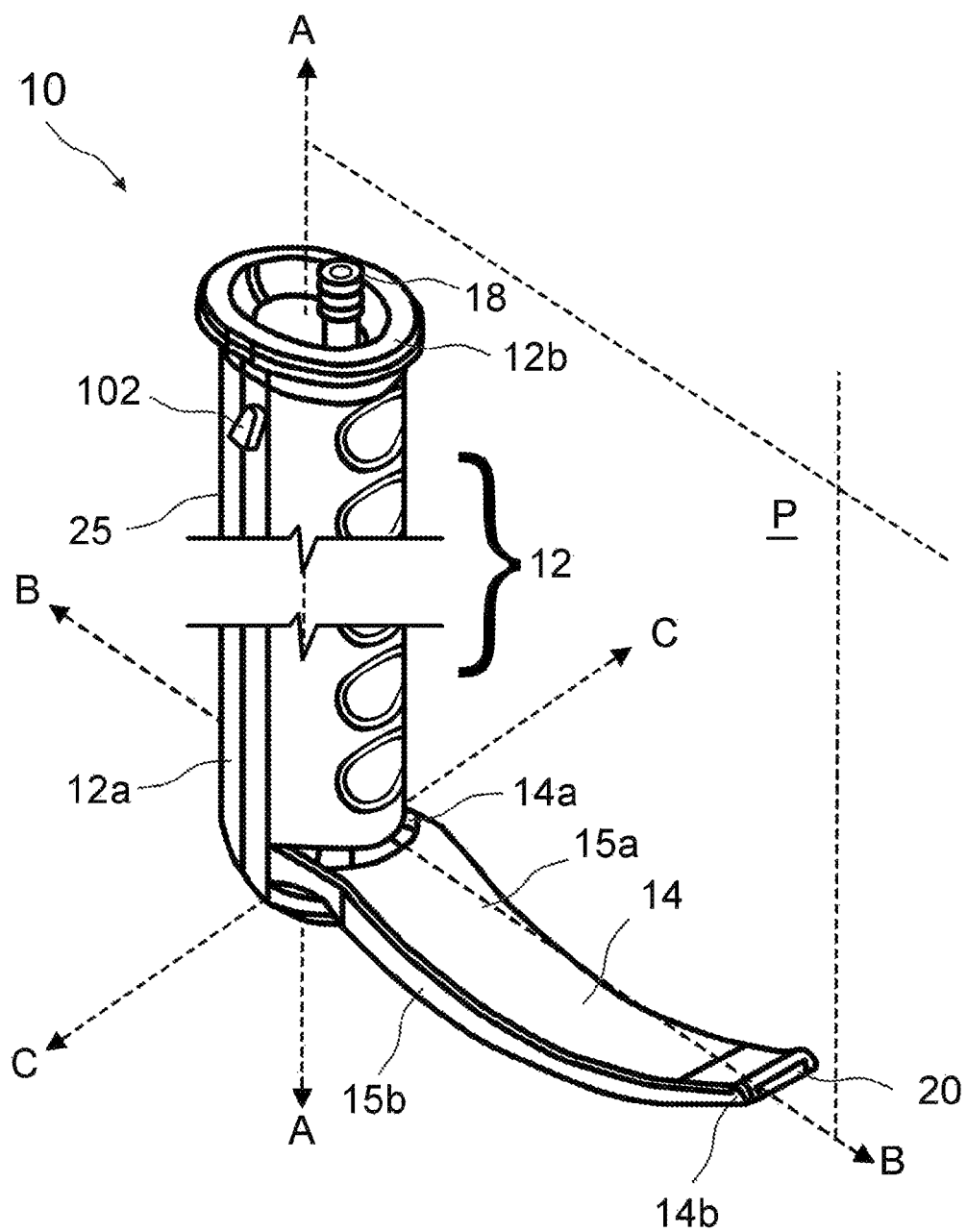
FIG. 1 is a perspective view of an embodiment of a laryngoscope device.
Figure 1A:
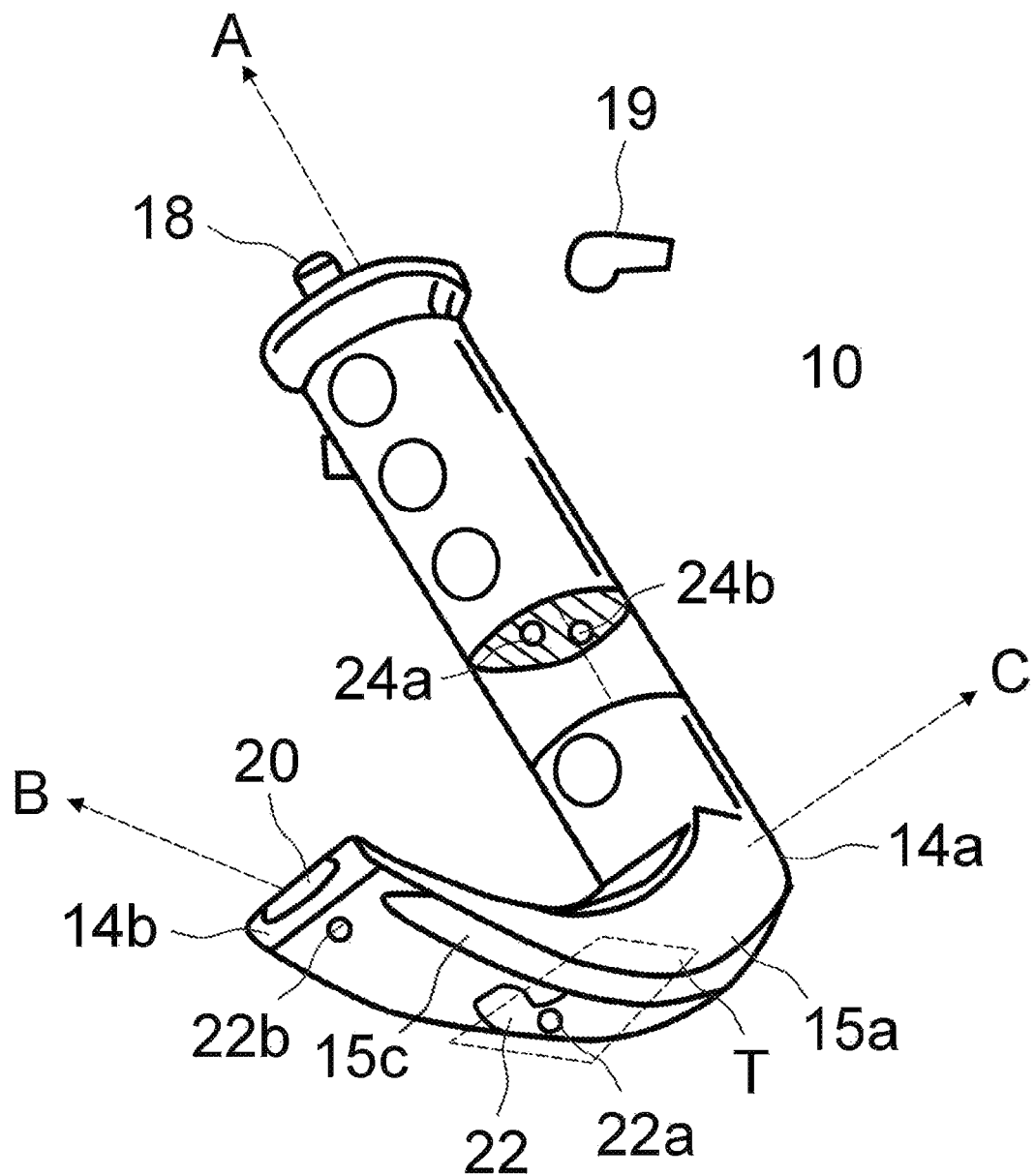
FIG. 1A is a perspective partial cross-section view of the device 10 in FIG. 1.

FIGS. 1, 1A, and 1B illustrate an embodiment of a laryngoscope device 10 providing for direct and indirect visualization of the glottis, vocal cords in, for example, an intubation or post-intubation process. In some examples, the device 10 includes a handle 12 and a blade 14. The handle 12 extends axially along a first axis A-A having a first end portion 12a and a second end portion 12b. The blade 14 has a proximal end portion 14a and a distal tip portion 14b at the opposite end of the blade. The proximal end portion 14a extends from the first end portion 12a of the handle with the proximal end portion 14a and the distal tip portion 14b spaced apart from one another in the direction of a second axis B-B perpendicular to the first axis to define a first plane P bisecting the handle 12.

The device 10 may have a proximal-to-distal overall length L1 of about 162 mm with the blade 14 having a proximal-to-distal axial length of L2 ranging from 105 mm to 110 mm. In a direction of a third axis C-C perpendicular to each of the first and second axes (A-A & B-B) the device 10 has lateral surfaces 15a, 15b disposed about the bisecting plane P. When viewed in the proximal-to-distal direction, the lateral surfaces of the device 10 may define an outer lateral surface 15a and an inner lateral surface 15b.

The laryngoscope device 10 can be inserted into the mouth and airway of a patient to view the glottis and/or vocal cords of the patient. The blade 14 preferably has a generally curved or arcuate profile as seen, for example, in the side view of FIG. 1B; and may have an outer curved profile like a Mac blade. Accordingly, the blade 14 has a concave upper or dorsal surface 16a and may have a convex lower or anterior surface 16b which are spaced apart to define a height H of the blade 14 between the dorsal and anterior surfaces 16a, 16b as shown in FIG. 1C.

The height H of the blade 14 varies and preferably decreases in the proximal-to-distal direction. In a preferred embodiment, the blade varies from a maximum height of 35 mm. to a minimum height of 3 mm. over the preferred axial length L2 of the blade 14. The height H is defined at least in part by difference between the first radius of curvature R1 of the dorsal surface 16a and the second radius of curvature R2 of the anterior surface 16b of the blade 16. The respective centers of curvatures D1, D2 of the dorsal and anterior surfaces 16a, 16b are preferably offset from one another. The first radius of curvature is may be constant over the length L1 of the blade 16 and in an embodiment, the first radius of curvature R1 is about 105 mm. The second radius of curvature R2 preferably varies and may decrease in the proximal-to-distal direction. In some embodiments, the second radius of curvature R2 ranges from about 132 mm to about 80 mm.

Moreover, the second radius of curvature R2 preferably varies in the lateral direction of the device 10 over the third axis C-C. In some examples, the second radius of curvature R2 decreases in the outer-to-inner lateral direction. Accordingly, the height H of the blade 14 varies and may decreases in the outer-to-inner lateral direction as seen for example in FIG. 1C. In some embodiments described herein, the height H of the blade 14 defines a step transition from a first height H1 to a second smaller height H2.

In the lateral direction of the third axis C-C, the step transition may define a transition in the blade 14 from an outer flange portion 17a to an inner flange portion 17b. For some embodiments described herein, the outer flange portion 17a has a greater height H1 than the height H2 of the inner flange portion 17b. In some aspects, the outer flange portion 17a defines a maximum height of 35 mm over the length of the blade. Additionally or alternatively, the outer flange portion 17a ranges in height from a maximum height of 35 mm. to a minimum height of 3 mm. Moreover, the inner flange portion 17b can define a maximum height of 17 mm over the length of the blade and may range in height from a maximum height of 17 mm to a minimum height of 5 mm.

Blade Cross Section Profile for Viewing

When inserted within the mouth and viewed from the proximal end 14a of the device 10, the height differential defines an asymmetric blade profile to frame a viewing notch or window W for direct viewing of the glottis and/or tongue. For example, schematically shown in FIG. 1D the blade 14 defines a substantially L-shape in cross-section with a viewing window W.

Another asymmetric blade 14' is shown in FIG. 1E that includes multiple height transitions in the lateral direction of the blade 14' in direction of the third axis C-C. Alternatively, the blade can define a symmetrical cross-sectional profile in manner described herein. For example, shown in FIGS. 1F and 1G are symmetric blades 14'', 14''' having a central window W framed respectively by either a substantially U-shaped or V-shaped anterior surface 16b. In each of the symmetrical embodiments, the height of the blade is maximized at the outer and inner portions 17a, 17b with a central portion having a decreasing height that is minimized at the center of the blade.

Fluid Ports

To facilitate proper insertion and positioning of the blade 14 and view of the glottis and/or vocal cords, the device provides for integrated and controllable suction to remove bodily fluids, e.g., blood, saliva, secretions, etc. in and around the blade 14. Thus, the blade 14 may include at least one, two, or more than two fluid ports for the intake fluid. In an alternative arrangement and/or application, the two fluid ports may be used for discharge of fluid such as for example, air. More specifically with reference to FIG. 1A, the device 10 includes an outlet 18 at the second end 12b of the handle 12 for coupling preferably to a negative pressure or vacuum source 19.

The outlet 18 can be embodied as a suction outlet 18 having a standard hose barb for connection to a vacuum source. At the distal tip portion 14a of the blade 14 is an inlet 20, which is placed in fluid communication with the outlet 18 for the intake and removal of fluid. Formed between the proximal end 14a and distal tip portion 14b of the blade 14 are one or more intermediate fluid intake ports 22 that are in fluid communication with the outlet 18 for the removal of fluid proximate preferred locations along the blade 14.

As described herein, the device 10 provides for one more internal visual-aid components, such as for example, lighting, video cameras or associated components to facilitate either direct or indirect visualization of, for example, the glottis and/or vocal cords, using the device 10. One or more of the fluid intake ports 22 are preferably sized and located proximate the operational ends of the visual-aid components, e.g., the camera lens or LED, to maintain a clean field of view for operation of the component. Application of the negative pressure or suction at the various ports is preferably controlled by a preferred fluid control valve assembly or arrangement 25 incorporated in the handle 12 having a preferably manually operated device, push-button, or controller 102 for operating the fluid control assembly 25.

Passageways

To provide for the fluid communication between the outlet 18 and the various fluid ports of the blade 14 and housing visual components, the device 10 includes one, two or more internal passageways between the fluid ports and the outlet 18.

As a fluid conduit or flow path of the device 10, the internal passageways of the device 10 are configured, dimensioned and/or shaped to facilitate desired fluid flow characteristics, flow rate, and/or pressure rates. Moreover, the internal passageways of the device 10 are located or arranged within the device 10 to provide for the preferred geometries or profiles of the blade 14 previously described in order to facilitate preferred insertion and viewing of the glottis and/or vocal cards as described herein.

Additionally, the preferred configurations, profiles, dimensions, shape and/or location of the passageways facilitate methods of formation and/or manufacturing of the device 10. Embodiments of the device 10 are preferably made in a preferred molding process in which two injection molded elements are formed and joined together in a preferred manner. In one preferred aspect, the device 10 is configured for single use. Accordingly, the device 10 is preferably formed in a manner and from a material such that the device 10 is disposable.

Figure 2:
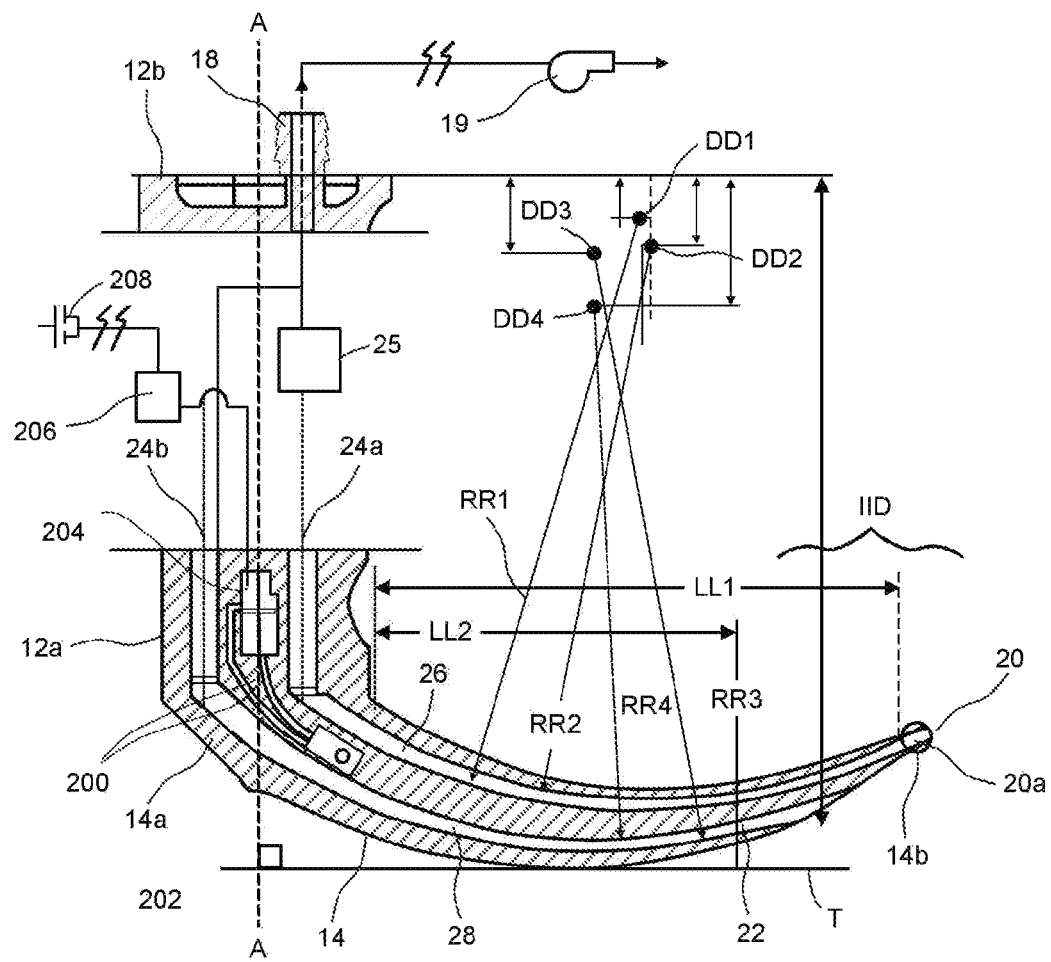
FIG. 2 is a partial cross-sectional schematic view of the device 10 of FIG. 1 along plane P.

FIG. 2 illustrates an embodiment of the device 10 including a handle 12 and blade 14. In this example, handle 12 includes a first internal (or handle) passageway 24a and at least a second internal (or handle) passageway 24b each extending from the first end portion 12a toward the second end portion 12b for fluid controlled communication with the outlet 18.

The blade 14 includes a first internal (or blade) passageway 26 formed therein having a length extending from the proximal end portion 14a to the distal tip portion 14b to provide fluid communication with each of the first internal passageway 24a of the handle 12 and the inlet 20 of the distal tip portion 14b of the blade 14. The blade 14 also includes a second internal (or blade) passageway 28 formed therein having a length extending from the proximal end portion 14a to at least one intermediate fluid port 22 for fluid communication with the second internal passageway 24b of the handle 12 and the intermediate fluid port 22.

FIG. 2A, a cross sectional view of the blade in FIG. 1B along the line IIA-IIA, illustrates an embodiments where each of the first and second internal passageways 26, 28 in the blade have a floor 30 and a ceiling 32 spaced apart in the direction of the first axis A-A from one another to respectively define a height HH1, HH2 and width WW1, WW2 in each of the internal passageways. Moreover, the floor 30 and ceiling 32 define a non-circular geometry for each of the first and second passageways 26, 28 in a cross-section of the blade 14 perpendicular to the second axis B-B. The respective heights HH1, HH2 of the first and second internal passageways 26, 28 vary over the length of each of the first and second passageways 26, 28. In some cases, each of the first and second internal passageways taper narrowly in the proximal-to-distal direction of the blade. In some embodiments of the device 10, the widths WW1, WW2 of the passageways remain constant over the length of the blade in the proximal-to-distal direction. Alternatively, the widths WW1, WW2 of the internal passageways 26, 28 can vary and may narrow in the proximal-to-distal direction of the blade.

As seen in FIG. 2, each of the first and second internal passageways 26, 28 may define an arcuate flow path within the blade 14. Accordingly, each of the floor 30 and the ceiling 32 define a radius of curvature that is preferably different from one another to provide the preferred tapering heights HH1, HH2 in each of the first and second internal passageways 26, 28 as previously described. In one example, the floor 30a of the first internal passageway 26 defines a radius of curvature RR1 of 120-125 mm and the ceiling 32a defines a radius of curvature RR2 of 115-120 mm. The radius of curvatures RR1, RR2 of the first internal passageway 26 are constant over its proximal-to-distal length LL1 within the blade 14.

The length LL1 of the first internal passageway 26 may range, in some examples, from 100 mm to 105 mm for fluid communication with the distal tip end 14b and its inlet 20. The floor 30b of the second internal passageway 28 defines a radius of curvature RR3 of 125 mm and the ceiling 32b defines a preferred radius of curvature RR4 of 110 mm. The radius of curvatures R1, R2 of the first internal passageway 26 may be constant over its proximal-to-distal length LL2 within the blade 14. The length LL2 of second internal passageway 28 may ranges from 55%-85% of the total blade length for fluid communication with a fluid port 22 for clearing the field of view of a visual aid component, such as for example, a camera lens or LED. In some embodiments of the blade 14, the internal passageway 26, 28 may have a variable radius of curvature over their length.

In some embodiments described herein, the internal passageways are positioned relative to one another and relative to one or more external surfaces of the device 10 to provide a desired blade geometry or facilitate manufacture or formation of the device 10. As shown in FIG. 2, the first and second internal passageways 26, 28 are axially spaced apart in the direction of the first axis A-A and concentric with one another. Accordingly, the floors 30a, 30b and ceilings 32a, 32b of each of the first and second passageways 26, 28 have respective centers of curvatures DD1, DD2, DD3, DD4 which are preferably off-set from one another in either the first or second axes A-A, B-B. In one aspect as shown in FIG. 2, the centers of curvature DD1, DD2 of the first internal passageway 26 are more distal than the centers of curvature DD3, DD4 of the second internal passageway 28.

When viewed in the proximal-to-distal direction, each of the first and second internal passageways 26, 28 define, in some examples, a cross-section that is non-circular, for example oblong, elliptical, or rectangular area for fluid to flow through. As schematically shown, for example in FIGS. 2B and 2C, each of the first and second internal passageways 26, 28 includes a planar outer wall 34 and a planar inner wall 36 relative to the respective inner and outer lateral surfaces 15a of the blade.

FIG. 2B, a cross-sectional view of the blade in FIG. 1B along line IIB-IIB, schematically shows the passageways 26, 28 proximate the handle 12 at the proximal end of the blade 14. FIG. 2C, cross-sectional view of a portion of the blade in FIG. 2 at IID, schematically shows the passageways 26, 28 proximate the fluid port 22 at the distal end of the second internal passageway 28 in the blade. Each of the inner and outer walls 34, 36 are spaced apart at the passageway width WW1, WW2 with each of the inner and outer walls extending parallel to the bisecting plane P to their floor-to-ceiling height HH1, HH2. Accordingly for each passageway, the inner and outer walls 34, 36 may have the same height. Alternatively, in either passageway, the inner and outer walls 34, 36 may have different heights, for example, wherein the first passageway the height of the outer wall 34a is greater than the height of the inner wall 36b.

In one embodiment of the device 10, the first internal passageway 26 may have a constant width WW1 of 10-15 mm and or about 12 mm over the proximal-to-distal length of the passageway with a height HH1 ranging from about 4-6 mm at the proximal end and narrowing to about 2 mm at the distal end of the passageway. Accordingly, in one aspect, the first internal passageway 26 defines a preferred width-to height-ratio ranging from about 2.5:1 to 7.5:1 in the direction from the proximal end portion to the distal tip portion.

Additionally or alternatively, the second internal passageway 28 may have a constant width WW2 of 2-5 mm and more preferably about 4.75 mm over the proximal-to-distal length of the passageway with a preferred height HH2 ranging from about 4-8 mm at the proximal end and narrowing to about 2.5 mm at the distal end of the passageway. Accordingly in one aspect, the second internal passageway 28 defines a width-to height-ratio ranging from 0.5:1 to 2:1 in the direction from the proximal end portion to the distal tip portion.

Generally, the first and second internal passageways 26, 28 are substantially located in the outer flange portion 17a of the blade 14. For example, with reference to FIG. 2B, the first internal passageway 26 extends across the bisecting plane P with at least 90% disposed in the outer flange portion 17a. Alternatively, the inner wall 36b of the first internal passageway 26 can be aligned with the bisecting plane P.

The first internal passageway 26 may be formed with its outer wall 34a spaced from the outer lateral surface 15a to define a minimum outer wall thickness TH1 of the outer flange portion 17a. The minimum outer wall thickness TH1 may range from about 4.5-5 mm and may be 4.75 mm and may be constant over the length of the outer flange portion 17a in the proximal-to-distal direction of the blade 14. The preferred minimum outer wall thickness TH1 provides for a preferred flange member 15c to be formed anteriorly of the first internal passageway 26 in the distal region of the blade distal of the end of the second internal passageway 28, as seen for example in FIG. 1I. The outer flange member 15c preferably ranges in thickness from 2 mm-6 mm. The inner lateral surface 36a of the first internal passageway defines the thickness TH2 of the inner flange portion 17b. Where the inner lateral surface 15b tapers toward the bisecting plane P, as seen for example in FIG. 1H, the inner flange thickness TH2 defines a narrowing thickness from the proximal end portion to the distal tip portion.

The outer and inner lateral surfaces 15a, 15b of the blade 14 are disposed about the bisecting plane P to define the width WTH of the blade. The width WTH of the blade 14 varies along the length of the blade, and may taper narrowly in the proximal-to-distal direction. In one embodiment, the width WTH of the blade at the distal tip portion 14b ranges from about 16-24 mm or 21.8 mm and the width WTH of the blade 14 at the proximal end portion 14a is about 25-33 or 31.75 mm.

In one embodiment, the inner lateral surface 15b tapers toward the bisecting plane P at a preferred angle β of about three to five degrees (3-5°). In another embodiment, the outer lateral surface 15a includes one portion extending parallel to the bisecting plane P with another portion tapering toward the bisecting plane P. In another embodiment, the inner lateral surface 15b tapers toward the bisecting plane P angle with respect to the first plane P and another portion extending parallel to the bisecting plane P. The inner lateral surface can transition from its taper to extending parallel to the plane P at the location of the operative end 40 of a visual aid component 40.

For example, where the blade 14 include a camera lens 40 located between the proximal end portion 14a and the distal tip portion 14b, the inner lateral surface 15b extending at the first taper angle β from the proximal end portion to the camera lens location 40 and extend parallel to the first plane P from the camera lens location 40 to the distal tip portion 14b. The outer surface 15b can extend parallel to the bisecting plane P from the proximal end portion 14a to the camera lens location 40 and define a second taper angle of about two to six degrees (2-6°) with respect to the bisecting plane P from the camera location 40 to the distal tip portion 14b.

At the distal tip portion 14b, the first internal passageway 26 is in fluid communication with the inlet 20. The inlet 20 has a width extending from the outer flange portion 17a to the inlet flange portion 17b with the inlet 20 crossing the bisecting plane P. The inlet preferably defines one of an oblong or elliptical geometry, as seen in FIG. 1C; and additionally or alternatively, the inlet 20 has a cross-sectional area greater than the cross-sectional area of the first internal passageway 26.

Figure 2D:
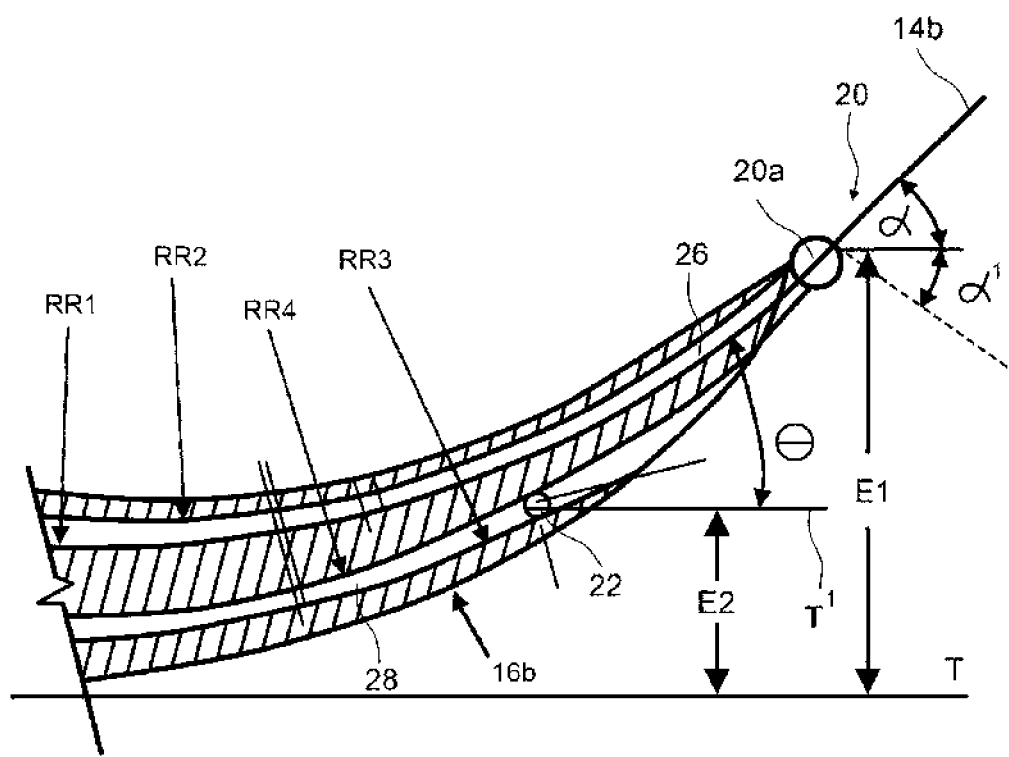
FIG. 2D is a detailed cross-sectional view of a portion of the blade in FIG. 2 at IID.

Moreover, with reference to FIG. 2D the distal tip portion 14b defines a transition passageway 20a defining the fluid communication between the inlet 20 and the first internal passageway 26. The transition passageway 20a defines a reduction in at least one of height and width of less than 10% from the inlet 20 to the first internal passageway 26. The transition passageway 20a can be angled with respect the first internal passageway 26 at an orientation angle α with respect to a tangential plane T extending perpendicular to the bisecting plane P (FIG. 2B) and tangential to the arcuate anterior surface 16b of the blade 14. In one orientation, the transition passageway 20a is angled with respect to the first internal passageway and the tangential plane T at a preferred downward orientation angle α' ranging from zero degrees to thirty degrees (0-(30) degrees). In one embodiment, the distal tip portion 14b defines an angle Θ of 24-28 degrees relative to the plane T', which is parallel to the tangential plane T. In another preferred aspect of the distal tip portion 14b, the inlet 20 is preferably disposed at a preferred elevation E1 from the tangential plane T of 48-52 mm. Additionally, the fluid port 22 is disposed at a preferred elevation E2 of 12-18 mm from the tangential plane T.

The second internal passageway 28 may be located anteriorly of the first internal passageway 26. With reference to FIGS. 2B and 2C, the outer wall 34b of the second internal passageway 28 may be located laterally between the outer wall 34 of the first internal passageway 26 and the bisecting plane P. The second internal passageway 36b can extend across the bisecting plane P with at least 90% disposed in the outer flange portion 17a. Alternatively, the inner wall 36b of the second passageway 28 is aligned with the bisecting plane P or further in the alternative be located between the outer wall 34b of the second passageway 28 and the bisecting plane P. By positioning the internal passageways 26, 28 in a manner relative to the lateral surfaces 15a, 15b of the blade, a wall thickness can be maintained to provide a desired structural thickness and/or strength along the length of the blade 14.

The second internal fluid passageway 28 is in fluid communication with the fluid port 22, which is located adjacent the operative end of a visual aid component 40, such as camera lens or LED positioned along the blade 14. The blade further may include other fluid ports defining a tissue release hole for removing tissue coming into contact with the blade 14. One tissue release hole 22a may be formed along the anterior surface 16b of the blade 14, as seen for example in FIG. 1A. The tissue release hole 22a may be located proximally 0.25-0.5 inches of the operative location 40 of the visual aid component and defining an angle of orientation ranging from zero to forty-five degrees (0°-45°) relative to the tangential plane T. Another tissue release hole 22b may be formed proximate the inlet 20 of the distal tip end 14b on the anterior surface 16b of the blade 14. The tissue release hole may be disposed within 0.5 inches of the inlet 20. The second tissue release hole 22b may define an angle of orientation ranging from zero to forty-five degrees (0°-45°) with respect to the tangential plane T.

The first and second internal passageways 26, 28 may be located to facilitate formation of a blade geometry including the outer and inner flange portions 17a, 17b and viewing window W as previously described. Moreover, the locations of the first and second internal passageways 26, 28 facilitate formation of the device 10.

Internal Passageways and Fluid Flow

Each of the first and second internal (blade) passageways 26, 28 of the blade 14 are placed in fluid communication with a suction source 19 by the first and second internal passageways 24a, 24b of the handle 12, which may be circular in cross-section. In other examples, the passageways 24a, 24b can be non-circular such as for example, oblong, elliptical, oval or rectangular. Each of the first and second internal (handle) passageways 24a, 24b of the handle 12 are preferably respectively formed integrally with the first and second (blade) internal passageways 26, 28 of the blade 14. The first and second internal (handle) passageways 24a, 24b extend preferably parallel to one another from first end of 12a the handle 12 in the direction of the second end 12b. The first and second internal passageways 24a, 24b each preferably define a centerline and the centerlines are preferably spaced apart and aligned with one another in a plane extending preferably parallel to the bisecting plane P, as seen for example in FIG. 2E. The parallel passageways can be alternately oriented provided they provide the fluid communication between the suction source 19 and the passageways 26, 28 of the blade 14.

The geometries and profiles of the internal passageways 24, 26, 28 provide for desired flow characteristics upon application of the negative pressure. The preferred first internal passageways 24a, 26 of the handle and blade 12, 14 defines a preferred internal volume that ranges from a minimum of 4100 mm³ to 11000 mm.³ The first internal passageway 26 of the blade 14 may define an internal volume ranging from 600 mm³ to 7200 mm³ and may range from 1450 mm³ to 4450 mm³ with a preferred ratio of LL1 to average equivalent diameter (equal circular diameter) of equivalent diameter of 4.75:1 to 18.5:1 or 10:1.

The first internal passageways 24a, 26 in the handle and the blade experience a pressure drop from the inlet 20 at the distal tip portion 14b from the outlet of the handle being of less than 4%, preferably ranging from 3-3.25% over the length of the passageway and is more preferably about 1.5% over the length of the blade when a negative pressure is applied at the outlet 18. Moreover, where the second internal passageways 24b, 28 in the handle and blade defines an internal volume ranging from a minimum 3900 mm³ to 6400 mm³ with the second internal passageway 28 in the blade ranging from 450 mm³ to 2600 mm³ or 700 mm³ to 1100 mm³ and a ratio of length LL2 to average equivalent diameter of preferably ranging from 4.75:1 to 17.25:1 or 14:1.

The second internal passageways 24b, 28 of the handle and blade 14 further preferably define a pressure drop from the fluid port 22 to the outlet 18 of less than 7% and more preferably about 6.25%-6.1%, more preferably less than 5% with a loss of about 4.5% through the blade section. For blade lengths L2 ranging between 170-240 mm, the total passageway length through the handle and blade may range from 205-215 mm.

Manufacturing

The device 10 may be constructed from a polycarbonate or thermoplastic material in an injection molding process. Alternatively, the device can be made from a 3-D printing process. The device can be made by fabricating two elements which respectively include complementary internal and external surfaces of the device, such that when the elements are joined together by any one of plastic welding, mechanical joining or chemical bonding, the elements form the device 10 including the handle 12, blade 14 and their internal passageways. Because it is anticipated that a polycarbonate device 10 will come into contact with bodily fluids, it is anticipated that the device 10 is a single use, preferably disposable device in some examples.

In one aspect of forming the device 10, two elements 10a, 10b are joined together along a split line SL by an appropriate joining process. Each of the complimentary elements 10a, 10b, include a portion of the handle 12 and a portion of the blade 14 such for each element 10a, 10b the handle 12 and blade 14 portions are integral with one another. In another aspect of the process of forming the device 10, each element 10a, 10b include one-half of the handle such that the split line SL is formed along the plane P bisecting the handle 12 as seen in FIG. 3A.

In another aspect of joining the elements 10a, 10b, the elements can be formed such that the complementary portions of the blade 14 are joined along a split line that is aligned with or parallel to the plane P bisecting the handle as seen for example in FIG. 3B. By locating the all of the second internal passageway 28 medially of the outer wall 32a of the first internal passageway, a single split line SL between the two elements 10a, 10b can be used to form the blade 14 and enclose the first and second internal passageways 26, 28.

In another example aspect, the split line SL can extend out of the bisecting plane P. For example, as shown in FIG. 3C, the second internal passageway 28 is laterally located between the outer and inner walls 34a, 36a of the first internal passageway 26 and the two elements 10a, 10b are joined along the split line SL having a portion that extends perpendicular to the bisecting plane P. Accordingly, an embodiment of the device 10 is formed with the handle being formed symmetric about the split line SL and the blade being formed asymmetric about the split line SL. FIGS. 3D and 3E show a blade 14 that is formed symmetrically about the plane P. The blade 14 show the first and second internal passageways 26, 28 symmetrically disposed about the plane P. Because of the location of the first and second internal passageways 26, 28, the device 10 includes two split line SL1, SL2 with a central element 10a joined to two lateral elements 10b, 10c enclosing the passageways 26, 28.

Fluid Control/Suction Assemblies

Shown schematically in FIGS. 4A-4F are various embodiments of a fluid control assembly 25 for use in the device 10. The control assembly 25 has at first operative configuration to allow application of the negative pressure or suction and flow of fluid through the first internal passageways 24a, 26 and to prevent flow through the second internal passageways 24b, 28. The control assembly 25 has at least a second operative configuration to allow application of the negative pressure and flow through the second internal passageways 24b, 28 and to prevent flow through the first internal passageways 24a, 26. The control assembly 25 can include a third configuration or home position in which fluid is not permitted to flow through either the first or second internal passageways.

In another operative configuration of the control assembly 25, fluid is permitted to flow through both the first or second internal passageways 24a, 24b, 26, 28 of the handle and blade. Moreover, the operation of the fluid control assembly 25 can provide for fixed fluid flow rates through the internal passageways or alternatively provide for adjustable fluid flow rates. Additionally, the fluid control assemblies can be configured for variable or differential flow rates through both the first or second internal passageways 24a, 24b, 26, 28 of the device 10.

Schematically shown in FIGS. 4A-4B is a first embodiment of a control assembly 25 embodied as a gate valve. The first and second internal passageways 24a, 24b extend parallel to one another in the direction of the first axis A-A with the passageways 24a, 24b coming together to form the outlet 18 in connection with the vacuum source 19. The control assembly 25 includes a plate 100 for selectively sliding in a proximal-distal direction of the second axis B-B perpendicularly through the first and second passageways 24a, 24b. The plate 100 includes two spaced apart through holes 104a, 104b. By sliding the plate 100 in the proximal-distal direction, the through holes 104a, 104b can be alternately and respectively aligned with the passageways 24a, 24b for select application of the negative pressure and suction to the first or second internal passageways 24a, 24b, 26, 28 of the handle and blade for fluid flow therethrough.

Coupled to opposite ends of the plate 100 are manual push-buttons 102a, 102b for respective depression by, for example, the index finger and thumb of the left hand of the user for one-hand use. For various embodiments shown herein, the push-buttons 102a, 102b can be alternatively configured as pull-rings 102a'. FIG. 4A shows the fluid control assembly for fluid flow through the first internal passageways 24a, 26 and FIG. 4B shows the fluid control assembly for fluid flow through the second internal passageways 24b, 28.

Figure 4C:
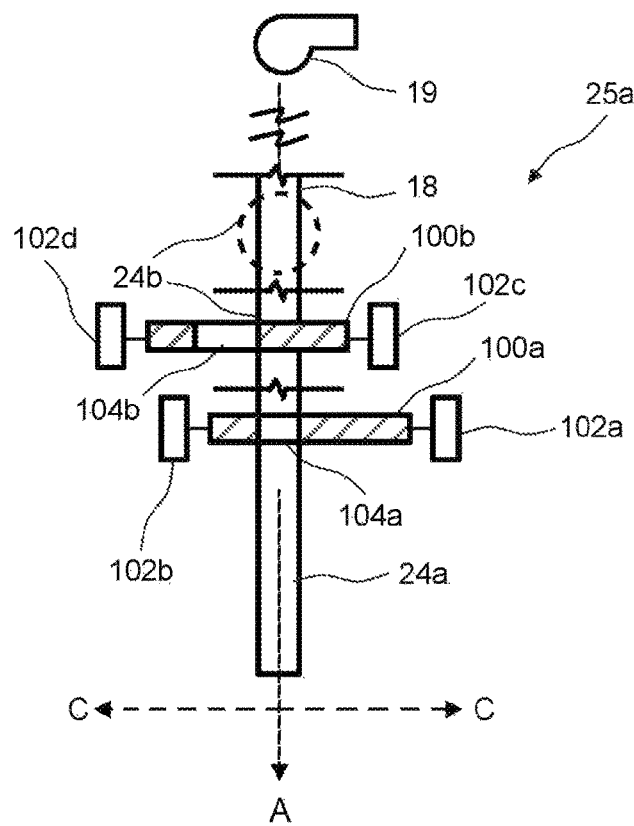

Schematically shown in FIG. 4C is an alternate fluid control assembly 25a embodied as an alternate gate valve arrangement for the passageway arrangement previously described. The assembly is viewed from the proximal end. The control assembly 25b includes a first plate 100a inserted through the first passageway 24a for sliding perpendicularly in the lateral direction of the third axis C-C. A second plate 100b is inserted through the second passageway 24b for sliding perpendicularly in the lateral direction of the third axis C-C. Each of the plates 100a, 100b include a through hole 104a, 104b for respective alignment with the respective passageway 24a, 24b and selective application of the suction source 19. The plates 100a, 100b can be independently operated from one another by depressing the opposed push-buttons 102a, 102b, 102c, 102d. FIG. 4C shows the fluid control assembly 25a for selected fluid flow through the first internal passageways 24a, 26 and the second internal passageways 24b, 28 closed off from the vacuum source 19.

Figure 4D:
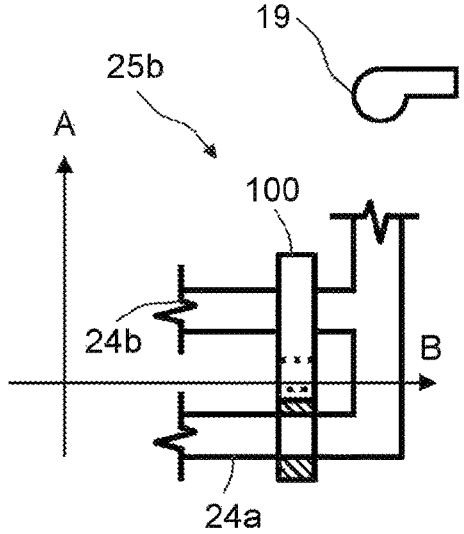
Figures 4C, 4D:
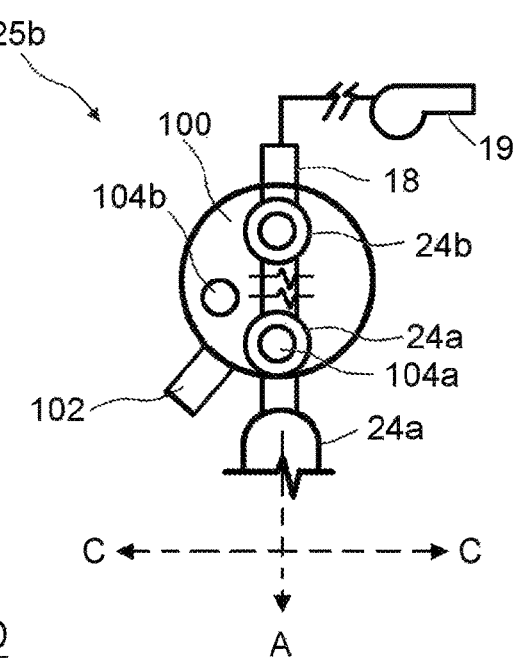

Schematically shown in FIG. 4D is an alternate fluid control assembly 25b embodied as a rotatable disc valve 100 for controlling through portions of the internal passageways 24a, 24b disposed parallel to the second axis B-B. The disc valve 100 includes at least two through holes 104a, 104b for selective alignment with the internal passageways 24a, 24b. The disc 100 includes a control arm 102 for selectively aligning the through holes 104a, 104b with the passageways 24a, 24b by rotating the disc about an axis parallel to the second axis B-B. Particularly shown in FIG. 4D is the fluid control assembly 25b for selected fluid flow through the first internal passageways 24a, 26 with the second internal passageways 24b, 28 closed off from the vacuum source 19.

Schematically shown in FIGS. 4E-4F is an alternate fluid control assembly 25c embodied as a rotatable disc valve 100 for controlling through portions of the internal passageways 24a, 24b disposed parallel to the first axis A-A. The disc valve 100 includes at least two through holes 104a, 104b for selective alignment with the internal passageways 24a, 24b. The disc 100 includes the a control arm 102 for selectively aligning the through holes 104a, 104b with the passageways 24a, 24b by rotating the disc 100 about an axis parallel to the first axis A-A. Particularly shown in FIGS. 4E-4F is the fluid control assembly 25b for selected fluid flow through the first internal passageways 24a, 26 with the second internal passageways 24b, 28 closed off from the vacuum source 19.

For the described fluid control assemblies 25, the desired flow or operational configuration can be realized by proper selection and adjustment in any one of the number of through holes 104, the spacing between the through holes 104, the size of the through holes or the adjustability in aligning the through holes 104 over the passageways 24a, 24b within the handle 12. The embodiments of the fluid control assemblies 25 shown and described in FIGS. 4A-4F may be mechanical arrangements for operation by one hand.

Alternate examples of the fluid control assemblies can include electrically operated valve assemblies controlled and operated by controls disposed about the handle 12 for preferred single handed operation.

Figure 6A:
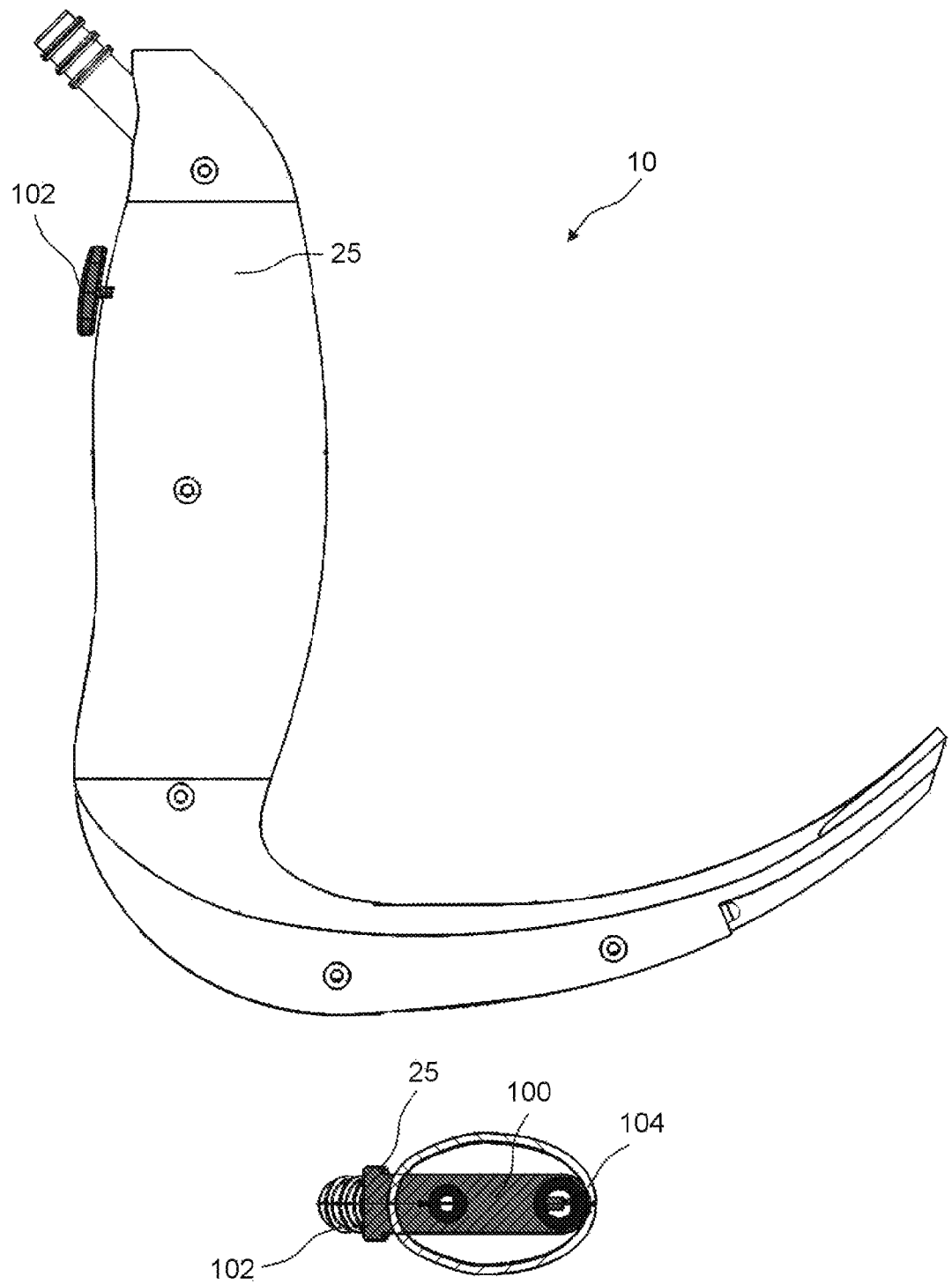
FIG. 6A is a side view of an embodiment of a laryngoscope device.
Figure 6B:
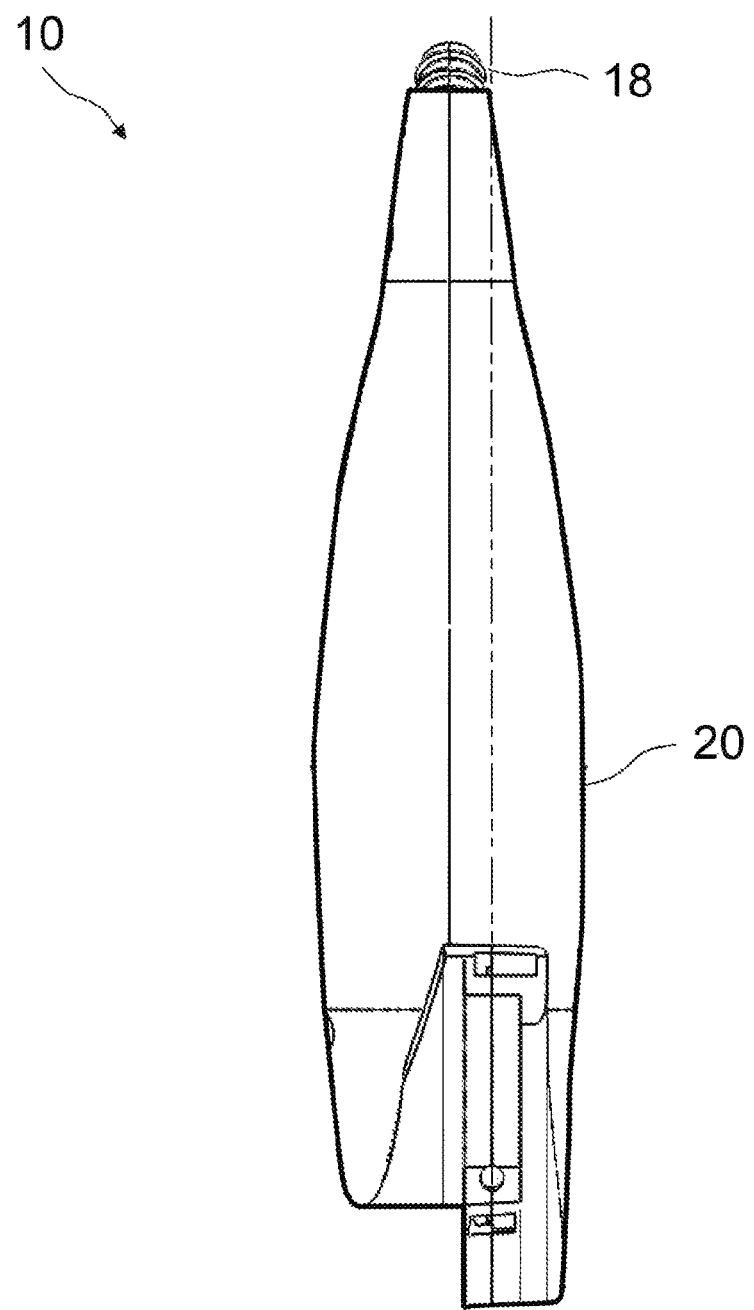
FIG. 6B is a front view of an embodiment of a laryngoscope device.
Figure 6C:
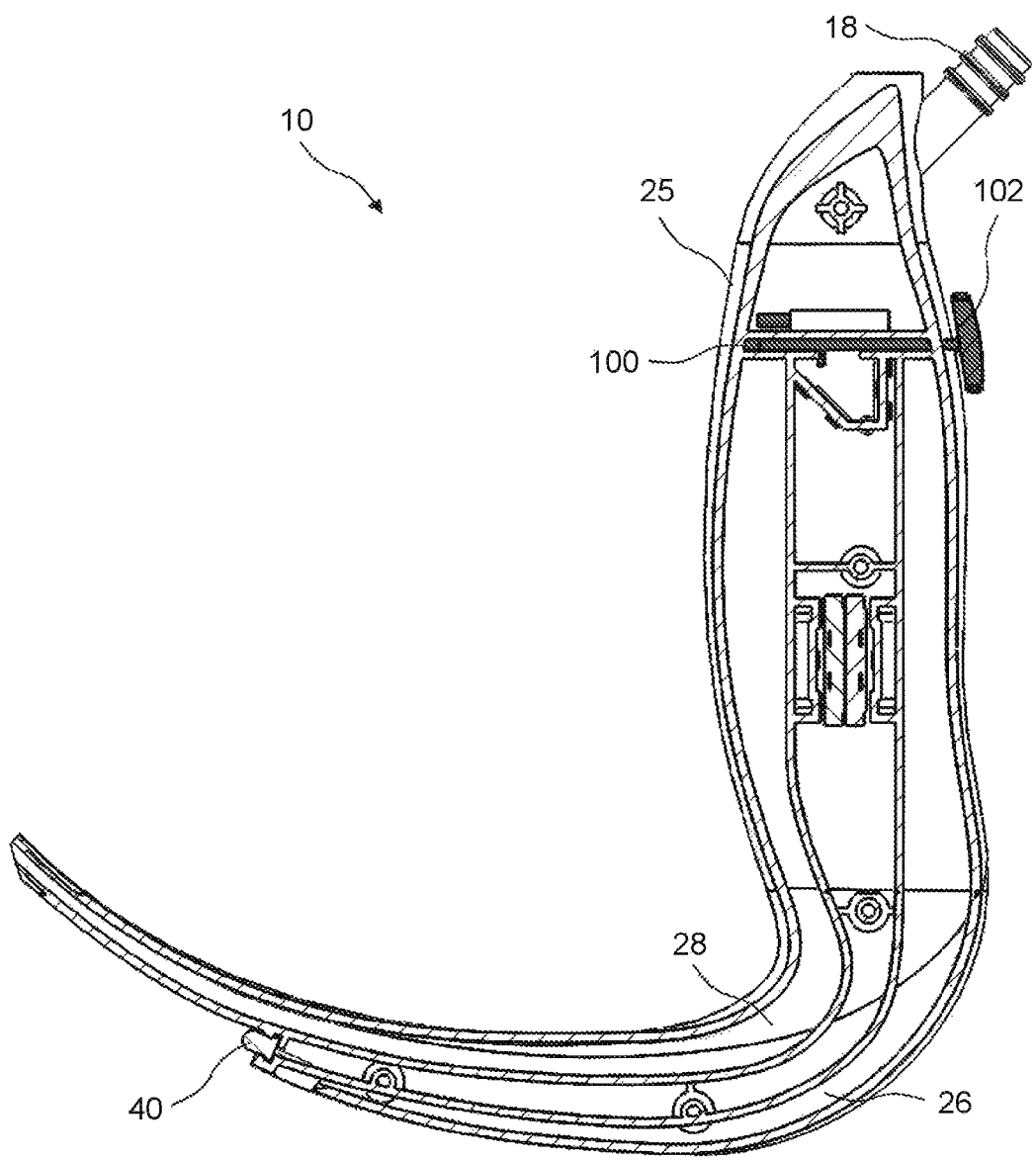
FIG. 6C is a cross sectional view of an embodiment of a laryngoscope device of FIG. 6A along the B-B axis.

FIGS. 6A-6D illustrate another embodiment of a laryngoscope according to the present invention that show the control assemblies. FIG. 6A illustrates a side view of the laryngoscope device 10 that illustrates an embodiment of a control assembly 25. The control assembly 25 is also illustrated in FIG. 6C and a cross sectional view of the control assembly 25 is illustrated in 6D. FIG. 6B illustrates a front view of this embodiment of the laryngoscope device 10 including the handle 12, blade 14, and fluid ports including intake 20.

FIG. 6C illustrates a cross sectional view of the laryngoscope device 10 and particular shows the control assembly 25 and associated integration with the fluid channels 28 and 26. The control assembly 25 includes a control arm 102 that may either or both rotate or translate in and out the plate 100 that covers the fluid channels 28 and 26.

FIG. 6D illustrates a cross sectional view of the control assembly 25 including the plate 100 and control arm 102. The through holes 104 illustrated demonstrate that by rotation of the control arm 102 the control plate 100 may rotate into position to allow fluid to flow through the channels 26 and 28. In other embodiments, the through holes 104 will not be aligned with the fluid path axis oriented parallel to each other, so that only one through hole 104 will be lined up with a channel at a time allowing only suction through one channel at a time.

In other embodiments, suction from each channel may have separate connections to the suction source that may be toggled through an external valve. In other embodiments, the control handle 100 may retract to allow suction through channel 28 and then rotate to allow suction through channel 26. In this example, the through hole 104 would be allowed distally from the channel 26 and then retraction of the control handle 102 would open up channel 28 and line up the through hole 104 in the same plane (but out of rotation). Then rotation of the control handle 28 would rotate the through hole 104 into alignment with the second channel 28 so that either, both, or none of the channels may be open at a time.

Figure 7A:
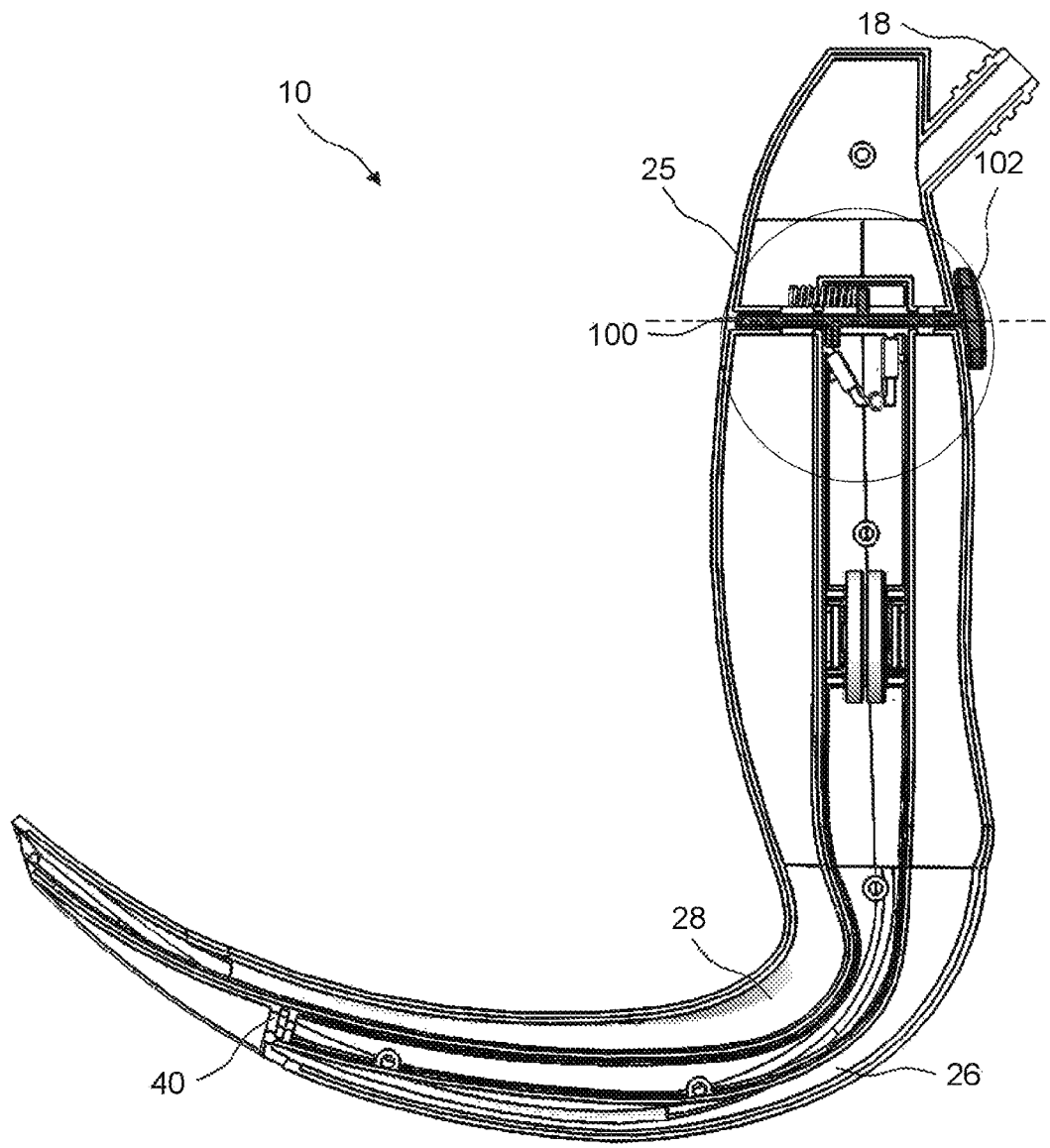
FIG. 7A is a cross sectional view of an embodiment of a laryngoscope device.

FIG. 7A illustrates a cross sectional view of the laryngoscope device 10 and particular shows the control assembly 25 with a retention spring 700 and associated integration with the fluid channels 28 and 26. The control assembly 25 includes a control arm 102 that may either or both rotate or translate in and out the plate 100 that covers the fluid channels 28 and 26. In some examples, the spring 700 will retain the plate 100 in a closed state to prevent fluid flow through the channels 28 and 26 until the operator moves control arm 102 to push or pull against the spring 700 to open one or both of the channels 28 and 26. In some examples, this will then only allow suction when the operator actively depresses the control arm 102.

FIGS. 7B-7C illustrate cross sectional views of the control assembly 25 including the plate 100 and control arm 102 and spring 700. In this example, the through holes 104 are opened by pulling the control arm 102 so that the through holes 104 line up with the channels 26 and 28 to allow suction and fluid flow.

FIGS. 7D-7E illustrate cross section views of the control assembly in a plane bisecting the device 10 along the control assembly 25. As illustrated, FIG. 7D shows the control arm 102 in an extended state and FIG. 7E illustrates the control arm 102 (and associated control plate 100) in a state that it is completely depressed inside the device 10. In some examples, extension (or retraction) of the control arm 102 will cause the through holes 104 to line up with the channels 26 and 28 and initiate suction. In other examples, depression of the control arm 102 (non-section state will be with control arm and control 100 plate extended) will cause the through holes 104 to line up with the channels 26 and 28 to initiate suction.

Examples of Medical Procedures

Figure 5:
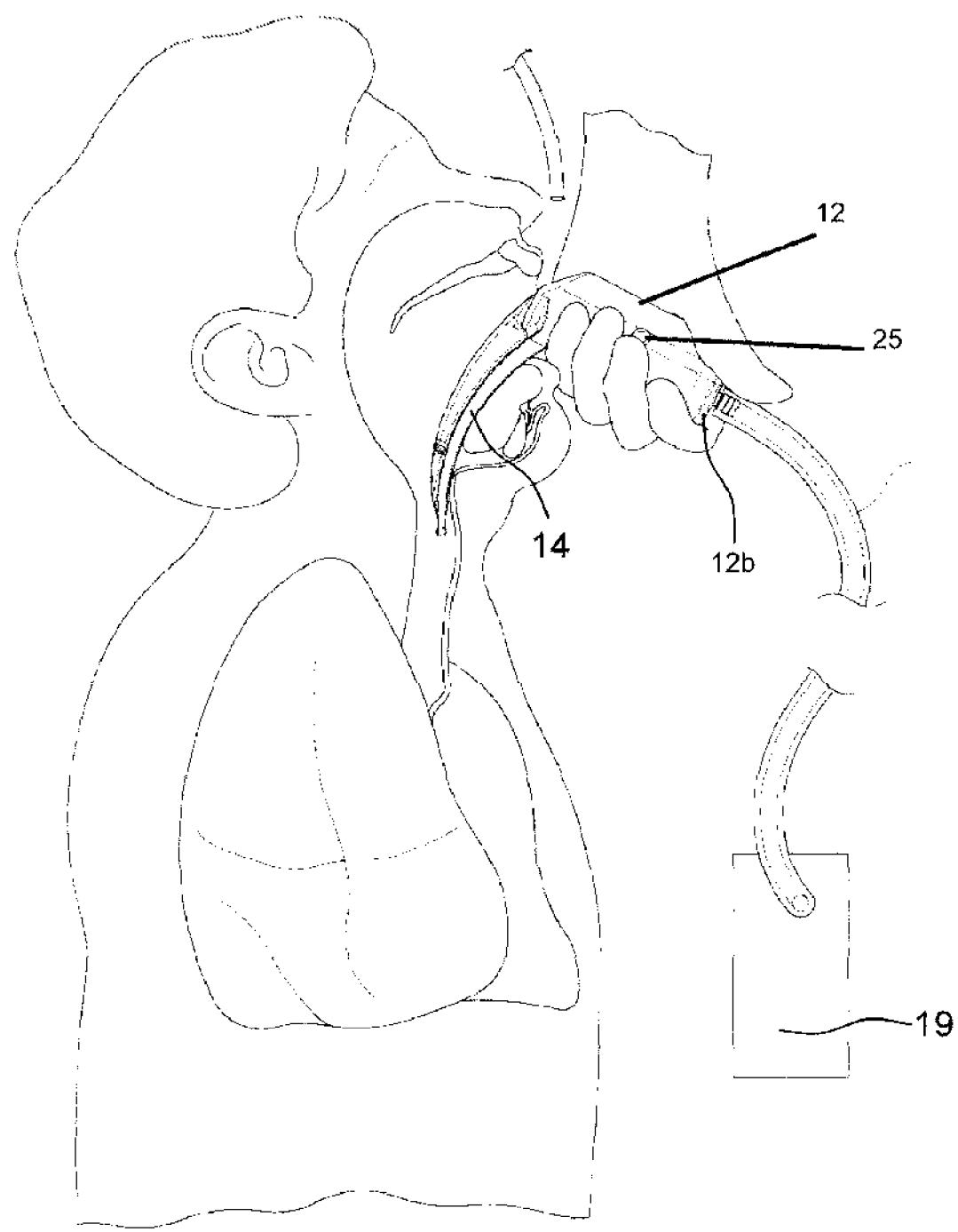
FIG. 5 is an illustration of using the device of FIG. 1.

The device 10, in some examples, is configured for one-handed operation and manipulation using the left hand with the blade 14 facing away from the operator. With reference to FIG. 5, the blade 14 lifts the epiglottis to expose the vocal cords indirectly. The outer flange portion 17a (FIGS. 1D, 2B) may be used for structural support to effectively push a patient's tongue from right to left in the mouth. The handle 12, in the second end portion 12b of the handle 12, includes a fluid control arrangement 25 for selection and controlled application of the negative pressure from the suction or vacuum source 19 to each of the first and second internal passageways 24a(FIG. 2), 24b(FIG. 2), 26 (FIG. 6C), 28 (FIG. 6C) of the handle and blade. The control arrangement 25 may be operable by the left hand; and more particularly, can be operated by a single finger, such as for example, the thumb or index finger.

Visualization Components

As previously noted, the device 10 may include or house visual-aid components, such as for example, lighting, video cameras, still picture cameras and/or associated components to facilitate either direct or indirect visualization of, for example, the glottis and/or vocal cords. In one example, the first end 12 of the handle 12 includes a third internal passageway 200, as seen in FIG. 2, which extends toward the second end 12a of the handle. The third internal passageway 200 of the handle 12 is in communication with a preferably third internal passageway 210 formed in the blade 14 preferably in the outer flange portion 17a, as seen in FIG. 2B, to extend from the proximal end portion 14a of the blade 14 in the proximal-to-distal direction. Alternatively, the third internal passageway 200 of the handle 12 is placed in communication with another passageway of the blade 14, such as for example, the second internal passageway 26.

The third passageway 210 of the blade 14 may terminate between the proximal end portion 14a and the distal tip portion 14b to define the location of the operative end 40 of a visual-aid component housed in the third passageway 210 for facilitating viewing of the glottis and/or vocal cords with the device 10. In one embodiment, a fiber optic wiring or harness can be disposed in the third passageway 210 of the blade 14 for locating a camera, LED or other light source at the preferred operative location. Moreover, the third internal passageway 210 terminates so as to locate the operative end 40 of the visual aid component adjacent the fluid port 22 for maintaining a clear field of view as previously described.

Referring again to the third internal passageway 200 of the handle 12 shown in FIG. 2, the passageway 200 preferably includes a first distal enlarged end 202 and a second proximal region 204. The passageway 200 and portions thereof may be sized in depth and/or width to house the visual-aid components. For example, a first video camera can be housed in the first enlarged area 202 and at least a secondary camera can be housed in the second enlarged region 204. The housing of multiple cameras facilitates the use of the device 10 to have multiple cameras of varying views.

Additionally housed in the third internal passageway 200 can be associated components, wiring or fiber optic cables including a microprocessor, power supply and/or wireless transmitter (Wi-Fi, Bluetooth® transmitter) 206 for powering and/or control of the visual aid components. Preferably housed and accessible about the handle 12 for single handed operation is a control button and/or switch 208. The control button(s) 208 can be configured for operation by either the thumb or single finger operation of the left hand of the surgeon, physician or operator. In one example, the physician can power on, select, direct and focus a camera with the thumb of the left hand and additionally transmit the images to a wirelessly connected display device (not shown).

The laryngoscope device 10 provides a medical device having an insertion member for directly and/or indirectly viewing into a human cavity and a handle for manually locating the insertion member within the cavity. Moreover the insertion member can incorporate two fluid flow passageways with suction control incorporated in the handle of the device for removing fluids and/or tissue from around the viewing area of the device or the visual aid components of the device. Accordingly, while the suction and manual control can be embodied in the laryngoscope 10, the described fluid flow passageways and control assemblies could be embodied in other medical devices for viewing

SELECTED EMBODIMENTS

Although the above description and the attached claims disclose a number of embodiments of the present invention, other alternative aspects of the invention are disclosed in the following further embodiments.

Embodiment

A laryngoscope device comprising: a handle extending axially along a first axis having a first end portion and a second end portion, the handle including a first internal passageway and at least a second internal passageway each extending from the first end portion to the second end portion; and an insertion member having a proximal end portion and a distal tip portion, the proximal end portion extending from the first end portion of the handle with the proximal end portion and the distal tip portion being spaced apart from one another in the direction of a second axis perpendicular to the first axis to define a first plane bisecting the handle portion, the insertion member including an inlet formed along the distal tip portion and at least one intermediate fluid port formed between the proximal end portion and the distal tip portion for intake of fluids, the insertion member including: a first internal passageway formed in the insertion member having a length extending from the proximal end portion to the distal tip portion for fluid communication with each of the first internal passageway of the handle and the inlet of the distal tip portion, the first internal passageway defining a non-circular passageway in a cross-section of the insertion member perpendicular to the second axis, the non-circular passageway having a floor and ceiling spaced apart from one another to define a height of the first internal passageway in the direction of the first axis, the height of the first internal passageway varying over the length of the first passageway, the first internal passageway having an inner wall and an outer wall spaced apart in a lateral direction of a third axis perpendicular to each of the first and second axes to define a width of the first internal passageway; and a second internal passageway formed in the insertion member anteriorly of the first internal passageway defining a length extending from the proximal end portion to the at least one intermediate fluid port for fluid communication with the second internal passageway of the handle and the at least one intermediate fluid port, the second internal passageway defining a non-circular passageway in a cross-section of the insertion member perpendicular to the second axis, the non-circular passageway having a floor and ceiling spaced apart from one another to define a height of the second internal passageway in the direction of the first axis, the height of the second internal passageway varying over the length of the second internal passageway, the second internal passageway having an inner wall and an outer wall spaced apart in the lateral direction to define a width of the second internal passageway, the outer wall of the second passageway being located laterally between the first plane and the outer wall of the first internal passageway; and a fluid control assembly incorporated in the handle for controlling fluid flow through each of the first and second internal passageways of each of the handle and the insertion member.

Embodiment

A laryngoscope device comprising: a handle extending axially along a first axis having a first end portion and a second end portion, the handle including a first handle passageway and at least a second handle passageway each extending from the first end portion to the second end portion; and a blade having a proximal end portion and a distal tip portion, the proximal end portion extending from the first end portion of the handle with the proximal end portion and the distal tip portion being spaced apart from one another in the direction of a second axis perpendicular to the first axis to define a first plane bisecting the handle portion, the blade including an inlet formed along the distal tip portion and at least one intermediate fluid port formed between the proximal end portion and the distal tip portion for intake of fluids, the blade including: a first blade passageway formed in the blade having a length extending from the proximal end portion to the distal tip portion in fluid communication with each of the first handle passageway of the handle and with the inlet of the distal tip portion, the first blade passageway defining a non-circular passageway in a cross-section of the blade perpendicular to the second axis, the first blade passageway having a floor and ceiling spaced apart from one another to define a height of the first blade passageway in the direction of the first axis, the height of the first blade passageway varying over the length of the first blade passageway, the first blade passageway having an inner wall and an outer wall spaced apart in a lateral direction of a third axis perpendicular to each of the first and second axes to define a width of the first blade passageway; and a second blade passageway formed in the blade anteriorly of the first blade passageway defining a length extending from the proximal end portion to the at least one intermediate fluid port for fluid communication with the second handle passageway and the at least one intermediate fluid port, the second blade passageway defining a non-circular passageway in a cross-section of the blade perpendicular to the second axis, the second blade passageway having a floor and ceiling spaced apart from one another to define a height of the second blade passageway in the direction of the first axis, the height of the second blade passageway varying over the length of the second blade passageway, the second blade passageway having an inner wall and an outer wall spaced apart in the lateral direction to define a width of the second blade passageway; and a fluid control assembly incorporated in the handle for controlling fluid flow through each of the first and second blade and handle passageways.

Embodiment

The device of an embodiment above, wherein the fluid control assembly includes any one of a gate valve and a disc valve.

Embodiment

The device of an embodiment above, wherein the length of the second blade passageway ranges from 55-85% of the total blade length.

Embodiment

The device of an embodiment above, wherein the inner walls of the first and second blade passageways are aligned with one another in the direction of the first axis.

Embodiment

The device of an embodiment above, wherein the inner wall of the second blade passageway is located laterally between the outer wall and the inner wall of the first blade passageway.

Embodiment

The device of an embodiment above wherein the outer and inner walls of the either one of the first and second blade passageways have different heights.

Embodiment

The device of an embodiment above, wherein the channel height of the either one of the first and second blade passageways taper narrowly from the mating plane to the inner and/or outer walls.

Embodiment

The device of an embodiment above, wherein the height of any one of the first and second blade passageways taper narrowly in the proximal end portion to the distal tip portion.

Embodiment

The device an embodiment above, wherein the width of the first blade passageway is constant in the proximal end portion to the distal tip portion.

Embodiment

The device of an embodiment above, wherein the first blade passageway defines a width to height ratio ranging from 2.5:1 to 7.5:1 in the direction from the proximal end portion to the distal tip portion.

Embodiment

The device of an embodiment above, wherein the first blade passageway defines a height ranging from 2 mm to 6 mm.

Embodiment

The device of an embodiment above, wherein the width of the first blade passageway ranges from 9 mm to 15 mm.

Embodiment

The device of an embodiment above, wherein the height of the second blade passageway tapers narrowly in the proximal end portion to the distal tip portion.

Embodiment

The device of an embodiment above, wherein the second blade passageway defines a height ranging from 1 mm. to 8 mm.

Embodiment

The device of an embodiment above, wherein the width of the second blade passageway is about 2-8 mm.

Embodiment

The device of an embodiment above, wherein the ceiling and the floor of each of the first and second blade passageways define a radius of curvature, the radius of curvature of the floor being greater than the radius of curvature of the ceiling.

Embodiment

The device of an embodiment above, wherein the radii of curvatures of the ceiling and the floor are fixed over the lengths of at least one of the first and second blade passageways.

Embodiment

The device of an embodiment above, wherein the center of curvature of the ceiling and the center of curvature of the floor are offset from one another in the first plane.

Embodiment

The device of an embodiment above, wherein the centers of curvature of the second blade passageway are spaced apart from the centers of curvature of the first blade passageway in the direction of the second axis, such that the centers of curvature of the second blade passageway are closer to the handle than the centers of curvature of the first blade passageway.

Embodiment

The device of an embodiment above, wherein the floor of the first blade passageway defines a preferred radius of curvature of 105-130 mm and the ceiling of the first blade passageway defines a preferred radius of curvature of 100-120 mm; and wherein the floor of the second blade passageway defines a radius of curvature of 114-140 mm and the ceiling of the second blade passageway defines a radius of curvature of 106-135 mm.

Embodiment

The device of an embodiment above, wherein the second end portion includes an outlet in fluid communication with the first handle passageway, the first blade passageway defining a pressure drop from the inlet at the distal tip portion to the outlet of the handle being less than 15% when a negative pressure source is applied at the outlet, the first internal passageway defining a ratio of length to average equivalent diameter of 4.75:1 to 18.5:1.

Embodiment

The device an embodiment above, wherein the first blade passageway of the outer flange portion of the blade defines an internal volume ranging from a minimum 600 $mm^2$. to 7200 $mm^2$.

Embodiment

The device of an embodiment above, wherein the second end portion includes an outlet in fluid communication with the first handle passageway, the second blade passageway defining a pressure drop from the at least one fluid port to the outlet of the handle being less than 20% when a negative pressure source is applied at the outlet, the second blade passageway defining a ratio of length to average effective diameter of 4.75:1 to 17.25:1.

Embodiment

The device of an embodiment above, wherein the second blade passageway of the outer flange portion of the blade defines an internal volume ranging from a minimum 450 $mm^2$. to 2600 $mm^2$.

Embodiment

The device of an embodiment above, wherein the inlet of the distal tip portion crosses the bisecting plane having one of an oblong or elliptical geometry.

Embodiment

The device of an embodiment above, wherein the inlet has an cross-sectional area less than the cross-sectional area of the first blade passageway of the outer flange, the distal tip portion defining a transition passageway between the inlet and the first internal passageway, the transition passageway defining a reduction in at least one of height and width of less than 10% from the inlet to the first internal passageway, the transition passageway being angled with respect to a plane parallel to the plane defined by the second and third axes.

Embodiment

The device of an embodiment above, wherein the at least one fluid port in fluid communication with the second blade passageway is located adjacent an operative end of a visual aid component.

Embodiment

The device of an embodiment above, wherein the visual aid component is one of a camera, fiber optic cable or LED.

Embodiment

The device of an embodiment above, wherein the at least one fluid port includes a tissue release hole formed along an anterior surface of the blade, the tissue release hole being located proximally 0.25-0.5 inches of the visual aid component and defining an angle of orientation ranging from zero to forty-five degrees (0°-45°).

Embodiment

The device of an embodiment above, wherein the visual aid component is position such that a viewing path of the visual aid component is at an angle ranging from 90°-45° to a fluid flow path of the distal portion of the second blade passageway at the at least one fluid port.

Embodiment

The device of an embodiment above, wherein the blade has a dorsal surface and anterior surface spaced apart from one another in the direction of the first axis to define a height of the blade ranging from 2-20 mm., the blade height varying in the lateral direction to define at least one transition between an outer flange portion and an inner flange portion.

Embodiment

The device of an embodiment above, wherein the blade includes an outer lateral surface extending along outer flange and inner lateral surface extending along the inner flange, the outer and inner lateral surfaces being disposed about the plane to define a width of the blade, the outer lateral surface and the outer wall of the first internal passageway being spaced apart to define an outer wall thickness, the outer wall thickness defining a constant thickness from the proximal end portion to the distal tip portion.

Embodiment

The device of an embodiment above, wherein the blade includes an outer lateral surface extending along outer flange and inner lateral surface extending along the inner flange, the outer and inner lateral surfaces being disposed about the plane to define a width of the blade, the outer lateral surface and the outer wall of the first internal passageway being spaced apart to define an outer wall thickness, the outer wall thickness includes a first portion having a constant thickness and a second portion having a narrowing thickness in the direction from the proximal end portion to the distal tip portion.

Embodiment

The device of an embodiment above, wherein the inner lateral surface and the inner wall of the first internal passageway are spaced apart to define the thickness of the inner flange, the inner flange thickness defining a narrowing thickness from the proximal end portion to the distal tip portion.

Embodiment

The device of an embodiment above, wherein the outer lateral surface includes a portion extending parallel to the first plane bisecting the handle, the inner lateral surface defining a first taper angle with respect to the first plane.

Embodiment

The device of an embodiment above, wherein the width of the blade varies along the length of the blade, the width of the blade tapering narrowly in the direction from the proximal end portion to the distal tip portion.

Embodiment

The device of an embodiment above, wherein the inner lateral surface extending at the first taper angle of about three to five degrees (3-5°) from the proximal end portion, the outer surface extending parallel to the first plane from the proximal end and defining a second taper angle of about two to six degrees (2-6°) with respect to the first plane.

Embodiment

The device of an embodiment above, wherein the width of the blade portion at the distal tip portion is 12-24 mm. and the width of the blade at the proximal end portion is 20-37 mm.

Embodiment

The device of an embodiment above, wherein the height varies in the lateral section defines an L-shaped viewing window of the device.

Embodiment

The device of an embodiment above, wherein the height varies in the lateral section defines a plurality of transitions with the second blade passageway located laterally between the inner and outer walls of the first blade passageway.

Embodiment

The device of an embodiment above, wherein the height varies in the lateral direction such that blade is symmetrical about the bisecting plane.

The device of an embodiment above, wherein the height varies in the lateral direction such that blade is asymmetrical about the bisecting plane.

Embodiment

The device of an embodiment above, wherein the anterior surface of the blade has at least one radius of curvature to defines a tangential plane perpendicular to the first plane bisecting the handle, the distal tip portion being disposed at an elevation from the tangential plane of 8-12 mm.

Embodiment

The device of an embodiment above, wherein the inlet defines an angle of orientation of 24-28 degrees relative to the tangential plane.

Embodiment

The device of an embodiment above, wherein a portion of the first and second handle passageways each define a centerline, the centerlines being spaced apart and aligned with one another in a second plane parallel to the first plane.

Embodiment

The device of an embodiment above, wherein the first and second handle passageways are circular.

Embodiment

The device of an embodiment above, wherein the first and second handle passageways are non-circular.

Embodiment

A method of forming a laryngoscope device comprising forming a first elements and a second element, each element having a blade portion and a handle portion integral with the blade portion; and forming a handle and a blade of the device with the first and second elements along a split line, the handle being symmetrical about the split line and the blade being asymmetrical about the split line.

Embodiment

The method of an embodiment above, wherein the forming the blade includes forming a first blade passageway and a second blade passageway, the second blade passageway being medial of an outer wall of the first blade passageway, the second element enclosing each of the first and second blade passageways.

Embodiment

A method of using a laryngoscope device on a patient comprises: withdrawing fluid through an inlet in fluid communication with a first passageway formed in an insertion member and through a fluid port in fluid communication with a second passageway formed in the insertion member, the inlet being located at a distal tip of the insertion member; and the fluid port being located between the distal tip and a proximal end portion of the insertion member; and alternating withdrawal between the inlet and the fluid port by a fluid control assembly located within a handle formed at the proximal end portion of the insertion member.

The method of an embodiment above, wherein the withdrawing of the fluid at the fluid port is in a direction from an outer flange portion of the blade toward an inner flange portion of the blade.

Embodiment

The method of an embodiment above, further comprising adjusting the flow in each of the first and second passageways, the flow in the first being different than the flow in the second.

Embodiment

The method of an embodiment above, wherein alternating the withdrawal includes operating a gate valve to alternate fluid between a first and second passageways in the handle which are in fluid communication with the first and second passageways.

Embodiment

The method of an embodiment above, wherein alternating the withdrawal includes operating a gate valve in the proximal-distal direction of the blade.

Embodiment

The method of an embodiment above, wherein alternating the withdrawal includes operating a gate valve in a direction perpendicular to the blade.

Embodiment

The method of an embodiment above, wherein alternating the withdrawal includes operating a rotary disc valve, the disc rotating about an axis parallel the proximal-to-distal direction.

Embodiment

The method of an embodiment above, wherein alternating the withdrawal includes operating a rotary disc valve, the disc rotating about an axis perpendicular to the proximal-to-distal direction and parallel the axis of the handle.

Embodiment

The method of an embodiment above, wherein the insertion member is a blade.

Embodiment

The laryngoscope device of an embodiment above, wherein the insertion member is a blade.

Embodiment

The device of an embodiment above, wherein the inlet of the distal tip portion has the smallest cross sectional area of the second blade passageway.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A laryngoscope device comprising:
    a handle extending axially along a first axis having a first end portion and a second end portion, the handle including a first internal passageway and at least a second internal passageway each extending from the first end portion to the second end portion;
    an insertion member having a proximal end portion and a distal tip portion, the proximal end portion extending from the first end portion of the handle with the proximal end portion and the distal tip portion being spaced apart from one another in a direction of a second axis perpendicular to the first axis to define a first plane bisecting the handle portion, the insertion member including an inlet formed along the distal tip portion and at least one intermediate fluid port formed between the proximal end portion and the distal tip portion for intake of fluids, the insertion member including:
        a first internal passageway formed in the insertion member having a length extending from the proximal end portion to the distal tip portion for fluid communication with each of the first internal passageway of the handle and the inlet of the distal tip portion, the first internal passageway defining a non-circular passageway in a cross-section of the insertion member perpendicular to the second axis, the non-circular passageway having a floor and ceiling spaced apart from one another to define a height of the first internal passageway in a direction of the first axis, the height of the first internal passageway varying over the length of the first passageway, the first internal passageway having an inner wall and an outer wall spaced apart in a lateral direction of a third axis perpendicular to each of the first and second axes to define a width of the first internal passageway; and
        a second internal passageway formed in the insertion member anteriorly of the first internal passageway defining a length extending from the proximal end portion to the at least one intermediate fluid port for fluid communication with the second internal passageway of the handle and the at least one intermediate fluid port, the second internal passageway defining a non-circular passageway in a cross-section of the insertion member perpendicular to the second axis, the non-circular passageway having a floor and ceiling spaced apart from one another to define a height of the second internal passageway in the direction of the first axis, the height of the second internal passageway varying over the length of the second internal passageway, the second internal passageway having an inner wall and an outer wall spaced apart in the lateral direction to define a width of the second internal passageway, the outer wall of the second passageway being located laterally between the first plane and the outer wall of the first internal passageway; and
    a fluid control assembly incorporated in the handle for controlling fluid flow through each of the first and second internal passageways of each of the handle and the insertion member.

2. A laryngoscope device comprising:
    a handle extending axially along a first axis having a first end portion and a second end portion, the handle including a first handle passageway and at least a second handle passageway each extending from the first end portion to the second end portion;

a blade having a proximal end portion and a distal tip portion, the proximal end portion extending from the first end portion of the handle with the proximal end portion and the distal tip portion being spaced apart from one another in a direction of a second axis perpendicular to the first axis to define a first plane bisecting the handle portion, the blade including an inlet formed along the distal tip portion and at least one intermediate fluid port formed between the proximal end portion and the distal tip portion for intake of fluids, the blade including:

a first blade passageway formed in the blade having a length extending from the proximal end portion to the distal tip portion in fluid communication with each of the first handle passageway of the handle and with the inlet of the distal tip portion, the first blade passageway defining a non-circular passageway in a cross-section of the blade perpendicular to the second axis, the first blade passageway having a floor and ceiling spaced apart from one another to define a height of the first blade passageway in a direction of the first axis, the height of the first blade passageway varying over the length of the first blade passageway, the first blade passageway having an inner wall and an outer wall spaced apart in a lateral direction of a third axis perpendicular to each of the first and second axes to define a width of the first blade passageway; and a second blade passageway formed in the blade anteriorly of the first blade passageway defining a length extending from the proximal end portion to the at least one intermediate fluid port for fluid communication with the second handle passageway and the at least one intermediate fluid port, the second blade passageway defining a non-circular passageway in a cross-section of the blade perpendicular to the second axis, the second blade passageway having a floor and ceiling spaced apart from one another to define a height of the second blade passageway in the direction of the first axis, the height of the second blade passageway varying over the length of the second blade passageway, the second blade passageway having an inner wall and an outer wall spaced apart in the lateral direction to define a width of the second blade passageway; and a fluid control assembly incorporated in the handle for controlling fluid flow through each of the first and second blade and handle passageways.

3. The device of claim 2, wherein the fluid control assembly includes any one of a gate valve and a disc valve.

4. The device of claim 2, wherein the length of the second blade passageway ranges from 55-85% of a total blade length.

5. The device of claim 2, wherein the inner walls of the first and second blade passageways are aligned with one another in the direction of the first axis.

6. The device of claim 2, wherein the inner wall of the second blade passageway is located laterally between the outer wall and the inner wall of the first blade passageway.

7. The device of claim 2 wherein the outer and inner walls of the either one of the first and second blade passageways have different heights.

8. The device of claim 7, wherein the height of the either one of the first and second blade passageways taper narrowly from a mating plane to the inner and/or outer walls.

9. The device of claim 2, wherein the height of any one of the first and second blade passageways taper narrowly in the proximal end portion to the distal tip portion.

10. The device claim 2, wherein the width of the first blade passageway is constant in the proximal end portion to the distal tip portion.

11. The device of claim 2, wherein the first blade passageway defines a width to height ratio ranging from 2.5:1 to 7.5:1 in the direction from the proximal end portion to the distal tip portion.

12. The device of claim 5, wherein the first blade passageway defines a height ranging from 2 mm to 6 mm.

13. The device of claim 6, wherein the width of the first blade passageway ranges from 9 mm to 15 mm.

14. The device of claim 2, wherein the height of the second blade passageway tapers narrowly in the proximal end portion to the distal tip portion.

15. The device of claim 2, wherein the second blade passageway defines a height ranging from 1 mm to 8 mm.

16. The device of claim 2, wherein the width of the second blade passageway is about 2-8 mm.

17. The device of claim 2, wherein the ceiling and the floor of each of the first and second blade passageways define a radius of curvature, the radius of curvature of the floor being greater than the radius of curvature of the ceiling.

18. The device of claim 17, wherein the radii of curvatures of the ceiling and the floor are fixed over the lengths of at least one of the first and second blade passageways.

19. The device of claim 17, wherein the center of curvature of the ceiling and the center of curvature of the floor are offset from one another in the first plane.

20. The device of claim 17, wherein the centers of curvature of the second blade passageway are spaced apart from the centers of curvature of the first blade passageway in the direction of the second axis, such that the centers of curvature of the second blade passageway are closer to the handle than the centers of curvature of the first blade passageway.

21. The device of claim 19, wherein the floor of the first blade passageway defines a preferred radius of curvature of 105-130 mm and the ceiling of the first blade passageway defines a preferred radius of curvature of 100-120 mm; and wherein the floor of the second blade passageway defines a radius of curvature of 114-140 mm and the ceiling of the second blade passageway defines a radius of curvature of 106-135 mm.

22. The device of claim 2, wherein the second end portion includes an outlet in fluid communication with the first handle passageway, the first blade passageway defining a pressure drop from the inlet at the distal tip portion to the outlet of the handle being less than 15% when a negative pressure source is applied at the outlet, the first internal passageway defining a ratio of length to average equivalent diameter of 4.75:1 to 18.5:1.

23. The device claim 2, wherein the first blade passageway of an outer flange portion of the blade defines an internal volume ranging from a minimum 600 mm$^2$ to 7200 mm$^2$.

24. The device of claim 2, wherein the second end portion includes an outlet in fluid communication with the first handle passageway, the second blade passageway defining a pressure drop from the at least one fluid port to the outlet of the handle being less than 20% when a negative pressure source is applied at the outlet, the second blade passageway defining a ratio of length to average effective diameter of 4.75:1 to 17.25:1.

25. The device of claim 2, wherein the second blade passageway of an outer flange portion of the blade defines an internal volume ranging from a minimum 450 mm$^2$ to 2600 mm$^2$.

26. The device of claim 2, wherein the inlet of the distal tip portion crosses the bisecting plane having one of an oblong or elliptical geometry.

27. The device of claim 2, wherein the inlet has a cross-sectional area less than the cross-sectional area of the first blade passageway of an outer flange, the distal tip portion defining a transition passageway between the inlet and the first internal passageway, the transition passageway defining a reduction in at least one of height and width of less than 10% from the inlet to the first internal passageway, the transition passageway being angled with respect to a plane parallel to the plane defined by the second and third axes.

28. The device of claim 2, wherein the at least one fluid port in fluid communication with the second blade passageway is located adjacent an operative end of a visual aid component.

29. The device of claim 27, wherein the visual aid component is one of a camera, fiber optic cable or LED.

30. The device of claim 27, wherein the second blade passageway includes a tissue release hole formed along an anterior surface of the blade, the tissue release hole being located proximally 0.25-0.5 inches of the visual aid component and defining an angle of orientation ranging from zero to forty-five degrees)(0°-45°.

31. The device of claim 28, wherein the visual aid component is positioned such that a viewing path of the visual aid component is at an angle ranging from 90°-45° to a fluid flow path of the distal portion of the second blade passageway at the at least one fluid port.

32. The device of claim 2, wherein the blade has a dorsal surface and anterior surface spaced apart from one another in the direction of the first axis to define a height of the blade ranging from 2-20 mm, the blade height varying in the lateral direction to define at least one transition between an outer flange portion and an inner flange portion.

33. The device of claim 32, wherein the blade includes an outer lateral surface extending along the outer flange portion and an inner lateral surface extending along the inner flange, the outer and inner lateral surfaces being disposed about the plane to define a width of the blade, the outer lateral surface and the outer wall of the first internal passageway being spaced apart to define an outer wall thickness, the outer wall thickness defining a constant thickness from the proximal end portion to the distal tip portion.

34. The device of claim 32, wherein the blade includes an outer lateral surface extending along the outer flange portion and an inner lateral surface extending along the inner flange, the outer and inner lateral surfaces being disposed about the plane to define a width of the blade, the outer lateral surface and the outer wall of the first internal passageway being spaced apart to define an outer wall thickness, the outer wall thickness includes a first portion having a constant thickness and a second portion having a narrowing thickness in the direction from the proximal end portion to the distal tip portion.

35. The device of claim 34, wherein the inner lateral surface and the inner wall of the first internal passageway are spaced apart to define the thickness of the inner wall, the inner wall thickness defining a narrowing thickness from the proximal end portion to the distal tip portion.

36. The device of claim 34, wherein the outer lateral surface includes a portion extending parallel to the first plane bisecting the handle, the inner lateral surface defining a first taper angle with respect to the first plane.

37. The device of claim 32, wherein a width of the blade varies along a length of the blade, the width of the blade tapering narrowly in the direction from the proximal end portion to the distal tip portion.

38. The device of claim 34, wherein the inner lateral surface extending at the first taper angle of about three to five degrees (3-5°) from the proximal end portion, the outer surface extending parallel to the first plane from the proximal end and defining a second taper angle of about two to six degrees (2-6°) with respect to the first plane.

39. The device of claim 32, wherein the width of the blade portion at the distal tip portion is 12-24 mm and the width of the blade at the proximal end portion is 20-37 mm.

40. The device of claim 32, wherein the height varies in a lateral cross-section to define an L-shaped viewing window of the device.

41. The device of claim 32, wherein the height varies in a lateral cross-section to define a plurality of transitions with the second blade passageway located laterally between the inner and outer walls of the first blade passageway.

42. The device of claim 32, wherein the height varies in the lateral direction such that blade is symmetrical about the bisecting plane.

43. The device of claim 32, wherein the height varies in the lateral direction such that blade is asymmetrical about the bisecting plane.

44. The device of claim 32, wherein the anterior surface of the blade has at least one radius of curvature to defines a tangential plane perpendicular to the first plane bisecting the handle, the distal tip portion being disposed at an elevation from the tangential plane of 8-12 mm.

45. The device of claim 32, wherein the inlet defines an angle of orientation of 24-28 degrees relative to the tangential plane.

46. The device of any one of the above claims, wherein a portion of the first and second handle passageways each define a centerline, the centerlines being spaced apart and aligned with one another in a second plane parallel to the first plane.

47. The device of claim 32, wherein the first and second handle passageways are circular.

48. The device of claim 32, wherein the first and second handle passageways are non-circular.

49. A method of forming a laryngoscope device comprising
forming a first element and a second element, each element having a blade portion and a handle portion integral with the blade portion; and
forming a handle and a blade of the device with the first and second elements along a split line, the handle being symmetrical about the split line and the blade being asymmetrical about the split line.

50. The method of claim 49, wherein the forming the blade includes forming a first blade passageway and a second blade passageway, the second blade passageway being medial of an outer wall of the first blade passageway, the second element enclosing each of the first and second blade passageways.

51. A method of using a laryngoscope device on a patient comprises:
withdrawing fluid through an inlet in fluid communication with a first passageway formed in an insertion member and through a fluid port in fluid communication with a second passageway formed in the insertion member, the inlet being located at a distal tip of the insertion member; and the fluid port being located between the distal tip and a proximal end portion of the insertion member; and alternating withdrawal between the inlet and the fluid port by a fluid control assembly located within a handle formed at the proximal end portion of the insertion member.

52. The method of claim 51, wherein the withdrawing of the fluid at the fluid port is in a direction from an outer flange portion of the blade toward an inner flange portion of the blade.

53. The method of claim 51, further comprising adjusting the flow in each of the first and second passageways, the flow in the first being different than the flow in the second.

54. The method of claim 51, wherein alternating the withdrawal includes operating a gate valve to alternate fluid between a first and second passageways in the handle which are in fluid communication with the first and second passageways.

55. The method of claim 54, wherein alternating the withdrawal includes operating a gate valve in the proximal-distal direction of the blade.

56. The method of claim 54, wherein alternating the withdrawal includes operating a gate valve in a direction perpendicular to the blade.

57. The method of claim 54, wherein alternating the withdrawal includes operating a rotary disc valve, the disc rotating about an axis parallel the proximal-to-distal direction.

58. The method of claim 54, wherein alternating the withdrawal includes operating a rotary disc valve, the disc rotating about an axis perpendicular to the proximal-to-distal direction and parallel the axis of the handle.

59. The method of claim 51, wherein the insertion member is a blade.

60. The laryngoscope device of claim wherein the insertion member is a blade.

61. The device of claim 14, wherein the inlet of the distal tip portion has a smallest cross sectional area of the second blade passageway.

* * * * *